US008733949B2

(12) United States Patent  
Chong et al.

(10) Patent No.: US 8,733,949 B2  
(45) Date of Patent: May 27, 2014

(54) SYSTEM FOR REPRESENTING COLORS INCLUDING AN INTEGRATING LIGHT CAPSULE

(75) Inventors: Patrick Chong, Mount Arlington, NJ (US); Michael Gutman, Livingston, NJ (US); Carl Minchew, Mountain Lakes, NJ (US); Hugh Fairman, Stillwater, NJ (US)

(73) Assignee: Columbia Insurance Company, Omaha, NE (US)

( * ) Notice: Subject to any disclaimer, the term of this patent is extended or adjusted under 35 U.S.C. 154(b) by 420 days.

(21) Appl. No.: 12/744,233

(22) PCT Filed: Dec. 22, 2008

(86) PCT No.: PCT/US2008/088011  
§ 371 (c)(1),  
(2), (4) Date: May 21, 2010

(87) PCT Pub. No.: WO2009/082737  
PCT Pub. Date: Jul. 2, 2009

(65) Prior Publication Data  
US 2010/0244700 A1  Sep. 30, 2010

Related U.S. Application Data

(60) Provisional application No. 61/016,539, filed on Dec. 24, 2007.

(51) Int. Cl.  
*G03B 21/14* (2006.01)  
*G03B 21/26* (2006.01)  
*F21V 1/00* (2006.01)  
*F21V 11/00* (2006.01)  
*B60Q 1/26* (2006.01)

(52) U.S. Cl.  
USPC ............... 353/94; 353/84; 362/227; 362/235

(58) Field of Classification Search  
USPC ........ 353/94, 100, 84–86; 315/113, 287, 294; 362/227, 235; 348/743  
See application file for complete search history.

(56) References Cited

U.S. PATENT DOCUMENTS 5,335,158 A     8/1994  Kaplan et al.  
5,982,957 A *  11/1999  DeCaro et al. ............... 382/312

(Continued)

OTHER PUBLICATIONS

International Search Report and Written Opinion issued in connection with corresponding International Application No. PCT/US2008/088011 on Feb. 19, 2009.

(Continued)

*Primary Examiner* — Georgia Y Epps  
*Assistant Examiner* — Jori S Reilly-Diakun  
(74) *Attorney, Agent, or Firm* — The H.T. Than Law Group

(57) ABSTRACT

Disclosed herein is a color display device that can be deployed at retail paint stores, kiosks, customers' offices or homes, airports, malls, etc. for rapid color and appearance prototyping. The color display device, which can be mobile, can display color under standardized lighting or simulated ambient lighting. The color display device can augment or replace a traditional paint chip rack or fan deck. The color display device can manipulate light sources additively and/or subtractively using an integrating light mixing capsule or chamber, special optics, mock objects and electronic control for color and appearance representation and for object illumination with desirable simulated ambient lighting.

37 Claims, 21 Drawing Sheets

(56) References Cited

U.S. PATENT DOCUMENTS

| | | | |
|---|---|---|---|
| 6,191,872 | B1 | 2/2001 | DeCaro et al. |
| 6,259,430 | B1 | 7/2001 | Riddle et al. |
| 6,513,937 | B1 * | 2/2003 | Dehmlow ............... 353/94 |
| 6,733,139 | B2 * | 5/2004 | Childers et al. ......... 353/94 |
| 6,888,636 | B2 | 5/2005 | Martino et al. |
| 6,985,163 | B2 | 1/2006 | Riddle et al. |
| 7,038,402 | B1 | 5/2006 | Adler et al. |
| 7,161,311 | B2 | 1/2007 | Mueller et al. |
| 7,161,313 | B2 | 1/2007 | Piepgras et al. |
| 7,186,003 | B2 | 3/2007 | Dowling et al. |
| 7,193,632 | B2 * | 3/2007 | Rice et al. ............. 345/597 |
| 2004/0263791 | A1 * | 12/2004 | Chen et al. ............. 353/31 |
| 2005/0162853 | A1 | 7/2005 | Jain |
| 2005/0232132 | A1 | 10/2005 | Ashdown et al. |
| 2006/0007406 | A1 * | 1/2006 | Adkins et al. ........... 353/82 |
| 2006/0081773 | A1 | 4/2006 | Rains et al. |
| 2006/0082732 | A1 | 4/2006 | Miwa et al. |
| 2007/0024824 | A1 * | 2/2007 | Damera-Venkata et al. ... 353/94 |
| 2007/0153026 | A1 | 7/2007 | Ashdown |
| 2011/0306021 | A1 * | 12/2011 | Mutimear ............... 434/98 |

OTHER PUBLICATIONS

European Search Report issued in connection with the corresponding European Patent Application No. 08863960.4 on Mar. 22, 2011.

Fryc, Irene et al. "LED-Based Spectrally Tunable Source for Radiometric, Photometric, and Colorimetric Applications." Optical Engineering 44(11), Nov. 2005. pp. 1-8.

Reichmann, Michael. "The Modulation Transfer Function Explained." Modulation Transfer Function. http://www.luminous-lanscape.com/tutorials/understanding-series/. 2007.

Paohuoa, Pedro et al. "Bright Approaches to Microcontroller-Based LED Drivers." Freescale Semiconductor, Inc. 2008.

Torres, Daniel. "Low-End 8-Bit MCUs Enable High-Brightness Automotive LED Control." Mechatropolis. 2008.

Howell, W.D. "An Overview of the Electronic Drive Techniques for Intensity Control and Colour Mixing of Low Voltage Light Sources such as LEDs and LEPS." Artistic License (UK) Ltd. London 2002.

* cited by examiner

100 # SYSTEM FOR REPRESENTING COLORS INCLUDING AN INTEGRATING LIGHT CAPSULE

FIELD OF THE INVENTION

This invention generally relates to a system of representing true colors under controlled ambient light including an integrating light capsule that can optically mix multiple color stimuli.

BACKGROUND OF THE INVENTION

Before purchasing paints, buyers typically are given a fan deck or palette comprising hundreds or thousands of paint chips, which represent a small portion of the available paint colors. The paint chips typically measure about 1¼ inch by 2 inches, and recently, the buyers can purchase larger paint chips of about 12 inches by 12 inches to assist the buyers with the mental projection of the colors to the walls. Additionally, the buyers may purchase small containers of about 2 ounces of the desired paints to paint larger swatches on the walls. Typically, the buyers start with small paint chips to narrow the choices and then move to larger paint chips and/or sample paints before choosing the final paint colors.

Recently, paint viewing or paint selection software, such as Benjamin Moore® Paints' Personal Color Viewer™ ("PCV") available either on the World Wide Web or as CD-ROM, has improved the paint selection process for the buyers. The PCV software displays on a computer screen a number of standard interior rooms with furniture, e.g., living room, dining room, bedrooms kitchen and bathroom, as well as the exteriors of a dwelling. The buyers can change the colors of the room, including ceiling, trim and upper and lower walls, at will to project the colors to the entire room. Additionally, digital images of the buyers' own dwellings can be manipulated by the PCV software to display the desired colors.

One possible drawback of the paint selection software is that the images are typically displayed on computer screens, which are limited to combinations of three RGB primary colors (red, green and blue), or four CMYK primary colors (cyan, magenta, yellow and black) for printers. Only a limited number of colors can be displayed and viewed, when only three or four primary colors are used. Similarly, a fan deck can only display several thousands of colors, while more than ten thousand paint colors are available.

Furthermore, both paint selection software and physical color chip fan deck cannot control the ambient light when paint colors are viewed by the consumers. It is known that colors can look different under different ambient illuminations, i.e., to a consumer a particular color can look one way under one ambient light and look differently under a different ambient light. This phenomenon is known as "color inconstancy." Color inconstancy is the change in color of a single physical color under different lights. For example, the colors we see outdoors are illuminated by the sun with a wide range of color temperature from sunrise to sunset. Indoor illumination or artificial light is rarely as bright as natural sunlight. Illumination is an important factor in viewing colors and the brightness of the environment has a measurable effect on colors viewed by people. This effect explains why a consumer sometimes thinks that a new paint applied at home looks different than that paint had looked at the store.

Another drawback of paint selection software and color chip fan deck is that they may be subject to "source metamerism." Two or more paints may have the same color appearance under one ambient lighting condition, but may appear to be different color under another ambient lighting condition. This is caused by the color pigment combinations of the paints can be different from each other. Paint selection software and color chip fan deck do not have the ability to vary ambient lighting condition.

The patent and scientific literatures disclose a number of attempts to address the representation of colors. A computer screen based color display system is disclosed in U.S. Pat. No. 6,717,584 B2. This reference discloses a method and apparatus for visualizing virtual paints on a computer-generated automobile. Reflectivity of the paints, which is caused by metal flakes or special effect pigments in the paints, and the angle at which the automobile is viewed affect the display of the virtual paints on the computer screen.

The walls in some public buildings, such as airports, have the capability of changing colors due to the lights that are projected on to them. For example, some of the walls in the Detroit airport are illuminated by LEDs. The colors and patterns on these walls can be changed at will by altering the outputs of the LEDs. No attempt is made to match the displayed color to the color of a real object or device independent color, and uniformity of colors on the walls is not a concern.

Methods of representing colors by devices are also described in U.S. Pat. Nos. 6,259,430 B1, 7,161,311 B2, 7,186,003 and 7,161,313. The '430 patent discloses a method of displaying colors that allegedly can control the metameric effect. This method divides the radiation spectrum into at least four wavelength bands and selects a single representative wavelength in each band. The intensity of each representative wavelength is selected, and a plurality of radiation beams at the selected intensities and representative wavelengths are generated and combined to produce the desired color. The '311 patent discloses devices such as light fixtures that combine multiple light emitting diodes (LEDs) to form a light source. The '311 patent discusses using a hollow cylindrical section to help mix the lights emitting from the LEDs. Similarly, researchers at the National Institute of Standards and Technology have used a hollow sphere to mix lights from a number of LED heads that are directly connected to the sphere. "LED-based Spectrally Tunable Source for Radiometric, Photometric and Colorimetric Applications." I. Fryc, S. Brown, G. Eppeldauer and Y. Ohno, Optical Engineering 44(11) 111309 (November 2005). The '003 and '313 patents discuss using processor-controlled LEDs with diffusing materials, e.g., transparent, translucent or semi-transparent materials, to produce color-changing effects.

U.S. Pat. Appl. Pub. No. 2006-0155519 A1 (hereinafter the '519 Application) discloses a full-size room that can uniformly display machine-generated colors on its walls to allow customers to view paint colors on full-size walls. The machine-generated colors are mixed in diffusers before illuminating the full-size walls. The disclosure of the '519 Application is incorporated herein by reference in its entirety.

However, there remains a need in the art for another system of displaying or simulating true paints that can be adapted to existing paint stores to assist the buyers in selecting paints.

SUMMARY OF THE INVENTION

The present invention is directed to a color display device that can be deployed at retail paint stores, kiosks, customers' offices or homes, airports, malls, etc. for rapid color and appearance prototyping. The color display device, which can be mobile, can display color under standardized lighting or simulated ambient lighting. The color display device can augment or replace a traditional paint chip rack or fan deck.

The inventive color display device can manipulate light sources additively and/or subtractively using an integrating light mixing capsule or chamber, special optics, mock objects and electronic control for color and appearance representation and for object illumination with desirable simulated ambient lighting.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

A plethora of choices awaits consumers when they shop for paints. Research has shown that human memories for colors are limited and fallible. Consumers may try to remember the colors, appearances and textures that they want. However, when the consumers arrive at retail paint stores, often they cannot recall the desired colors. Consumers may also bring physical samples to the retail stores and attempt to match the colors and textures. Samples, however, can be too cumbersome, large or heavy to bring to the store. Customers may also try to measure the colors with a digital device and bring their numerical equivalents to the retail stores. Digital devices are not widely available, and can be difficult to use. Moreover, the digital devices are only as accurate as the number of primary colors that these devices use to measure colors and as the number of colors that are contained in the color library within each device.

In accordance with the present invention, a color display device can be set up at retail paint stores, mall kiosks or any mobile stations or vehicles that can rapidly and accurately display colors and textures (flat, satin, eggshell, matte, gloss, semi-gloss, smooth, rough etc.) of available paints, under controlled ambient lighting. Customers can also experiment with colors and textures by varying the ambient lighting, and view colors suggested by the color display device that are harmonious or emotionally compatible to the colors that the consumers had selected. The inventive color display device can supplement or replace the traditional color chip rack or fan deck.

Figure 1:
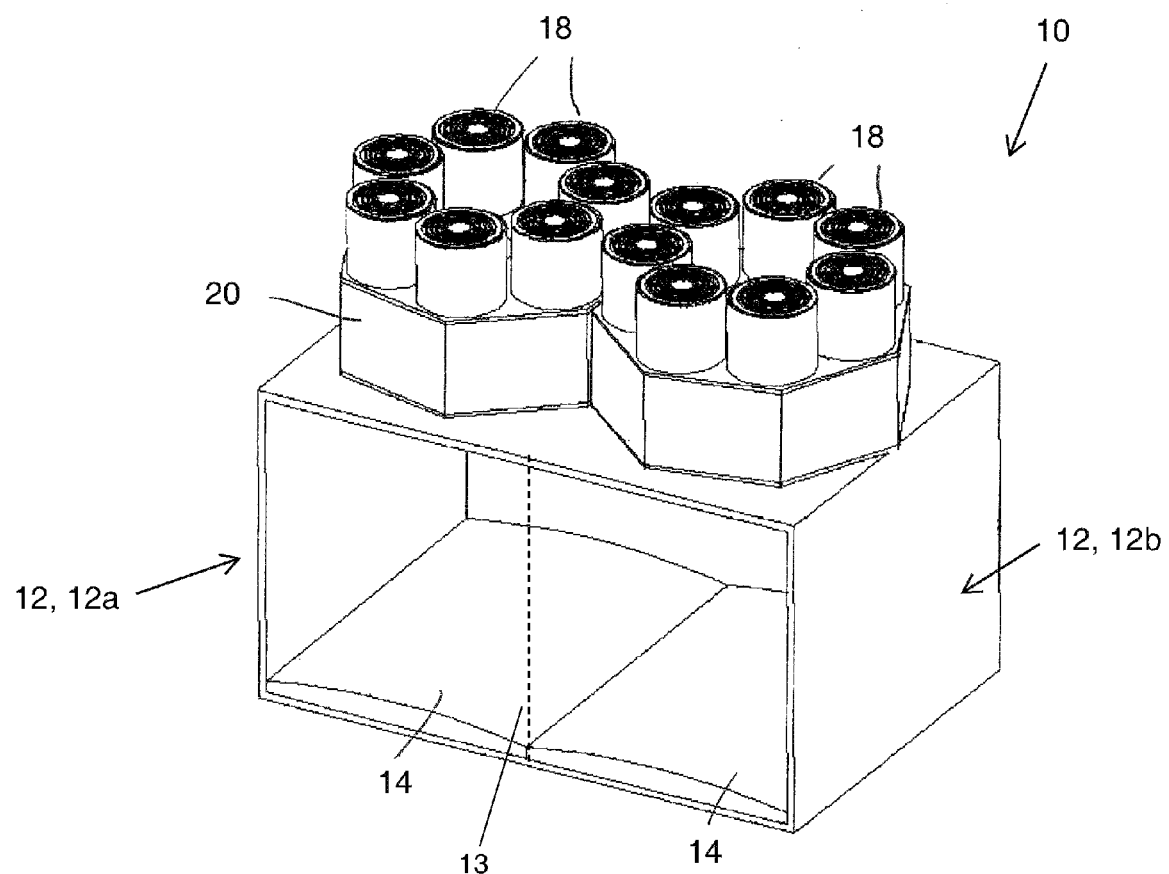
FIG. 1 is a schematic, perspective view of the color display device of the present invention.

The inventive color display device is illustrated schematically and is referred as element 10 in FIG. 1. Device 10 can have any dimensions, so long that it can be positioned within the desired locations, e.g., retail paint stores, mall kiosks, airports and train stations, etc. In one preferred embodiment, color display device 10 can be three feet long, two feet deep and about three feet tall, so that it can fit on a table top or countertop. In another preferred embodiment, color display device 10 can have the size of a room or being sufficiently large to allow the viewers to step inside color display device 10.

Color display device 10 comprises at least one viewing chamber 12, where a mixed, uniform light representing any colors illuminates the chamber. As shown, device 10 has two chambers 12a and 12b. One chamber can show the colors selected by the consumer and the other chamber can suggest other harmonious or emotional colors to the consumers. Each chamber 12 also has a textured surface 14 preferably positioned opposite to the entrance of the mixed, uniform light. Textured surface 14 can have a surface roughness that when illuminated can accurately display the finish or sheen of paint, i.e., flat, matte, satin, eggshell, semi-gloss, high gloss, smooth and rough. The textured surface 14 is also a diffusing surface, i.e., enhanced to mix light. Other surfaces of chambers 12 can also be textured similarly to surface 14 or different therefrom to show different paint finishes. A vertical boundary strip 13 can be provided between adjacent textured surfaces 14 to minimize spillover from two light sources. In one configuration, a loose-leaf flip is used where both sides of a loose-leaf has a textured surface 14, such that a consumer can easily change the surface roughness or texture of textured surface 14 by flipping the loose-leaf. Additionally, three-dimensional objects, such as mock furniture, can be positioned inside chambers 12. More preferably, objects with curved or round surfaces, such as spheres or donut-shapes, with or without surface roughness to show flat, matte, eggshell, satin, semi-gloss, high gloss, smooth and rough finishes can be positioned inside chambers 12 to illustrate the sheen of the displayed color to the consumers.

Each chamber is optically connected to an integrating light mixing capsule 16 (not visible in FIG. 1), which is optically connected to a plurality of primary light modules 18. Each primary light module 18 represents a unique color or a unique band of visible or invisible electromagnetic radiation, described below. Primary light modules 18 are connected to housing 20, which is connected to chamber 12, as shown in FIG. 1. Housing 20 also encloses integrating light mixing capsule 16.

Figure 2:
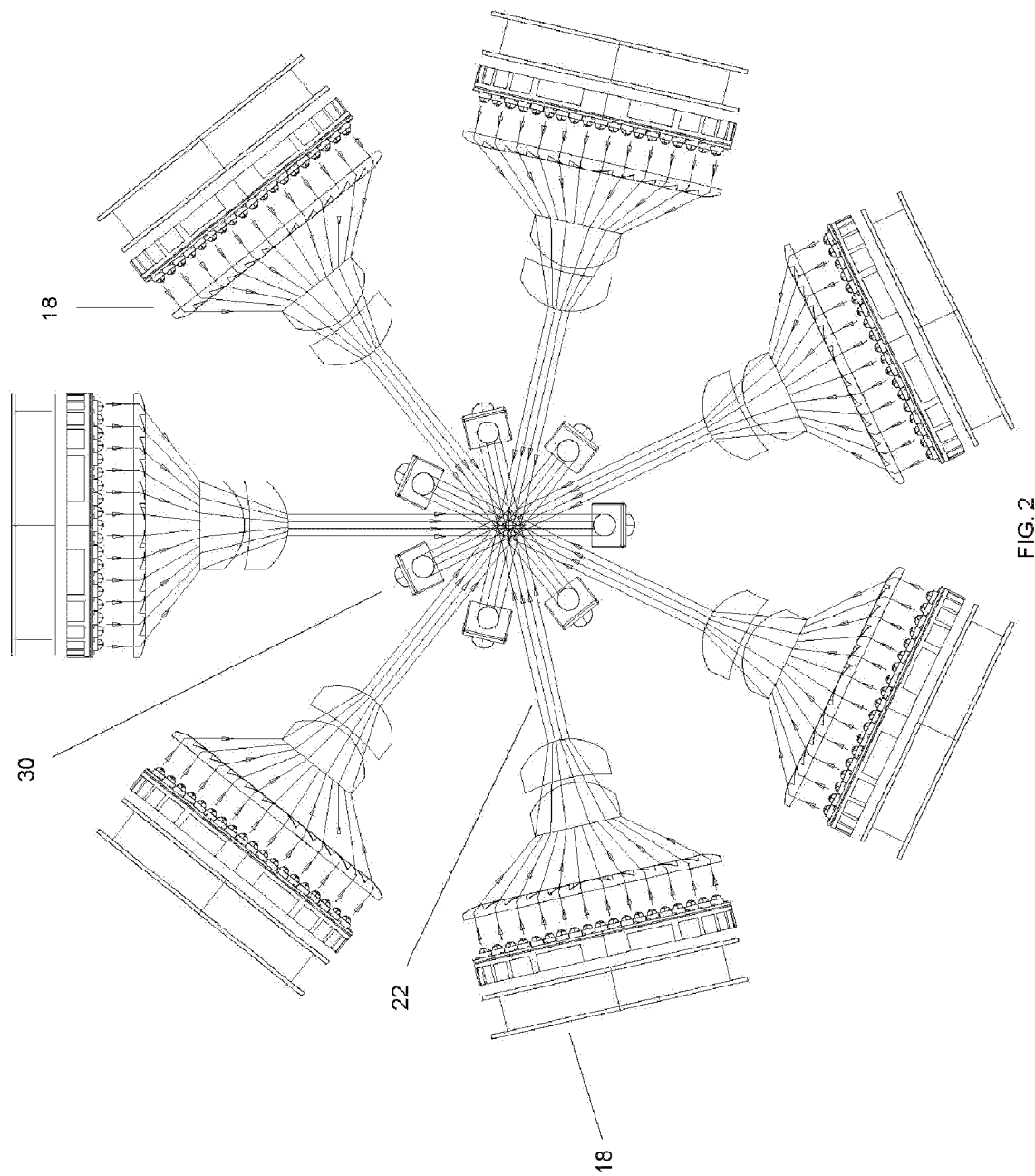
FIG. 2 is a schematic, top view of the primary light modules.
Figure 3:
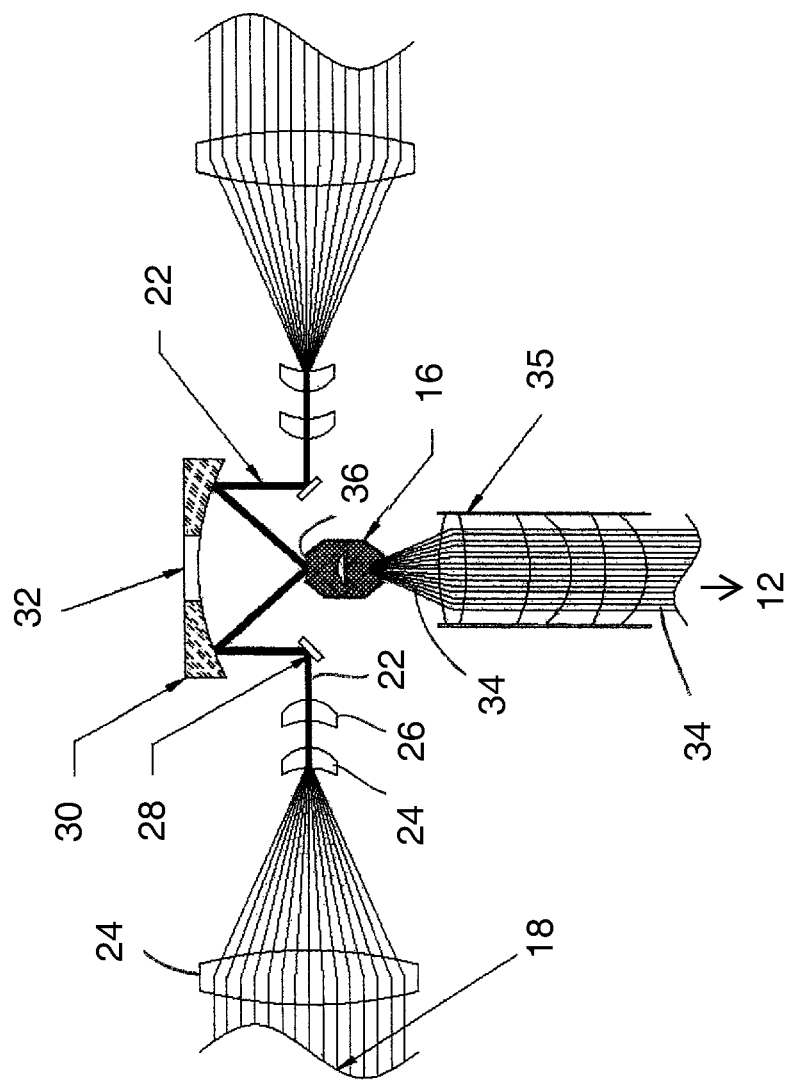
FIG. 3 is a schematic, top view of two primary light modules, associated optics and an integrating light mixing capsule.

Referring to FIG. 2, primary light modules 18 are shown emitting primary light beams 22 into integrating light mixing capsule 16. Each primary light module emits a unique primary light of known color. Primary light modules 18 can be arranged in any orientation, e.g., parallel to each other as shown in FIG. 1 or radially toward each other as shown in FIG. 2, or at any angle(s) relative to each other so long as optical lenses or mirrors can direct emitting light beams 22 into integrating light mixing capsule 16. For example, as shown in FIG. 3, an emitting light beam 22 is focused or collimated by focusing lens 24. The focused light can be further conditioned through one or more conditioning lens 24, 26 before being redirected at mirror or optical reflector 28 toward curved reflector 30 before being finally re-directed toward integrating light mixing capsule 16. Optical sensors, such as spectral and/or luminosity sensors, discussed below, for each light beam 22 can be deployed at 26. As shown in FIG. 3, a plurality of emitting light beams 22 are directed by curved reflector 30 into integrating light mixing capsule 16, where the light beams are mixed before exiting as mixed, uniform light 34, which represents a device dependent color and illuminates chamber 12 to show the consumers a paint color, as discussed above. Mixed light 34 may pass through lens/filter 35 and/or other exit optical devices 35 to enlarge and/or condition the beam before reaching chamber 12. Curved reflector 30 can have any curvature, and preferably has a parabolic shape. Curved reflector 30 may optionally have aperture 32 to allow other lights to enter integrating light mixing capsule 16. In one example, controlled ambient light enters integrating light mixing capsule 16 through aperture 32.

While a single curved reflector 30 can direct multiple light beams 22 into integrating light mixing capsule 16, each light beam 22 can have its own dedicated curved reflector 30, as shown in FIG. 2. In the arrangement shown in FIG. 2, each light beam 22 is passed between two curved reflectors 30 to minimize cross-talk among the light beams, i.e., interferences caused by the proximity of multiple beams having different colors or frequencies.

Figure 4A:
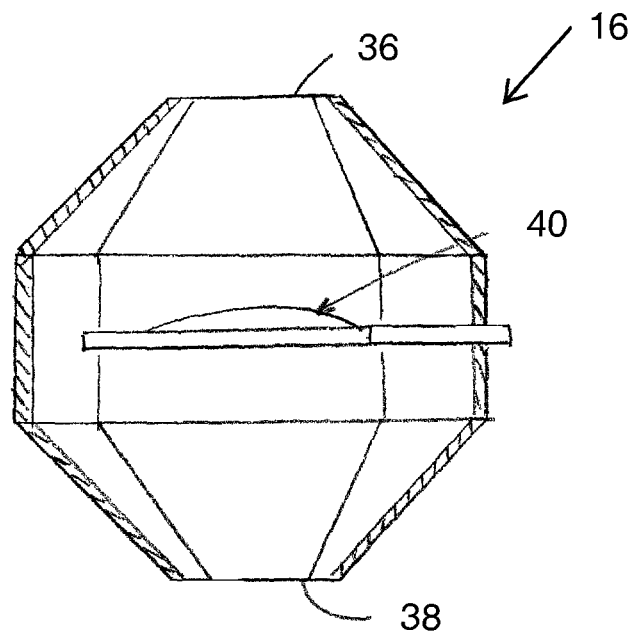
FIG. 4A is a cross-sectional view of the integrating light mixing capsule.
Figure 4B:
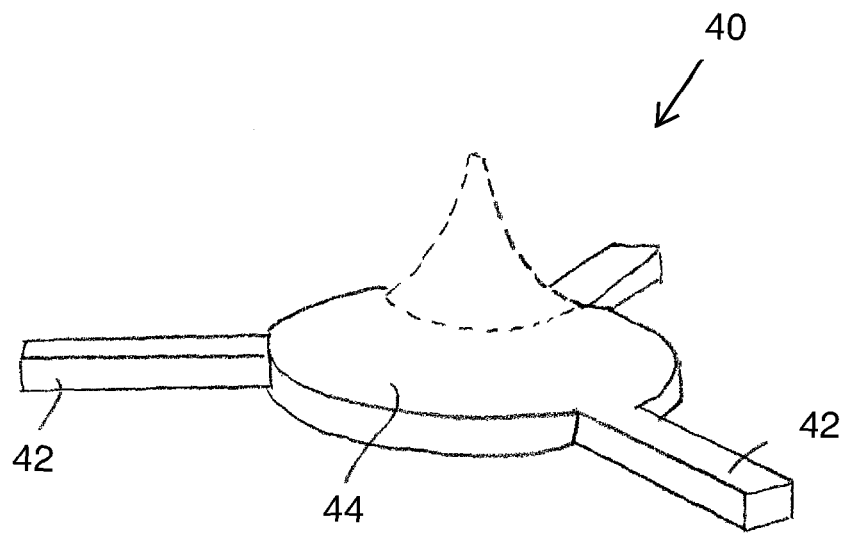
FIG. 4B is a perspective view of an optical baffle.

Referring to FIGS. 4A and 4B, an embodiment of integrating light mixing capsule 16 is illustrated in detail. Integrating light mixing capsule 16 preferably has a hollow polyhedron shape and can have as many faces or facets as necessary. The faces of the polyhedron reflect light beams 22 that entered the mixing capsule to mix the beams. Mixing capsule 16, which can also be spherical or elliptical, has entrance port 36 adapted to receive light beams 22 and exit port 38 to emit mixed, uniform light 34. Integrating light mixing capsule 16 also has baffle 40, which is preferably positioned between entrance port 36 and exit port 38 to minimize the chance of a light beam 22 being able to exit mixing capsule 16 without being reflected therewithin and mixed. As shown, baffle 40 has three legs 42, which are connected to the sides of mixing capsule 16. Baffle 40 can have any number of legs 42, so long as it can be connected to mixing capsule 16 in a stable manner, and it allows lights to pass between the legs. The inside surfaces of mixing capsule 16 and baffle 40 can be coated by a reflective coating to increase reflectivity while minimizing the loss of light through light transmission through the walls of the mixing chamber and the baffle. Suitable coatings include, but are not limited to, barium sulfate or titanium dioxide. Furthermore, the inside surfaces of mixing capsule 16 should be matted, so that light would reflect from these matted surfaces hemispherically to increase the mixing effects. The center 44 of baffle 40 can have any shape including dome, as illustrated in FIG. 4A and pointed, as illustrated in FIG. 4B. Center 44 of baffle 40 should be larger than both entrance port 36 and exit port 38.

Lenses 24, 26, 35, mirror/reflectors 22, 30 and other optical devices employed may in one embodiment have poor modulation transfer function, which is counter to the art of good lens design. Poor modulation transfer function (MTF) results in a poor resolving power and a poor contrast thereby blur the combined primary lights 22 to mix or homogenize these lights. In one embodiment, the preferred MTF is less than about 0.7, more preferably less than about 0.6 and more preferably less than about 0.5.

Exit optics located at 35 in another embodiment may comprise a projection lens with an internal beam restriction mask and adjustable aperture. These optical devices confine the projected mixed light to a fixed target, e.g., the bottom surface of chamber 12 or textured/curved surface 14, and to control the edge sharpness of the projected shape. Additionally, a filter mount can also be provided, which is sized and dimensioned to receive a number of filters, including but not limited to, neutral density filters to extend dynamic range and to balance luminance for comfortable viewing levels, center gradient filter to compensate for undesirable light edge fall-off that may occur at close projection distances (e.g., at large beam angle), spectral modification filters to remove undesirable wavelengths. Spectral modification filters can also be used to enhance primary light source, and would be mounted to intercept the primary light sources 22 before they enter the integrating light mixture capsule 16.

Figure 7A:
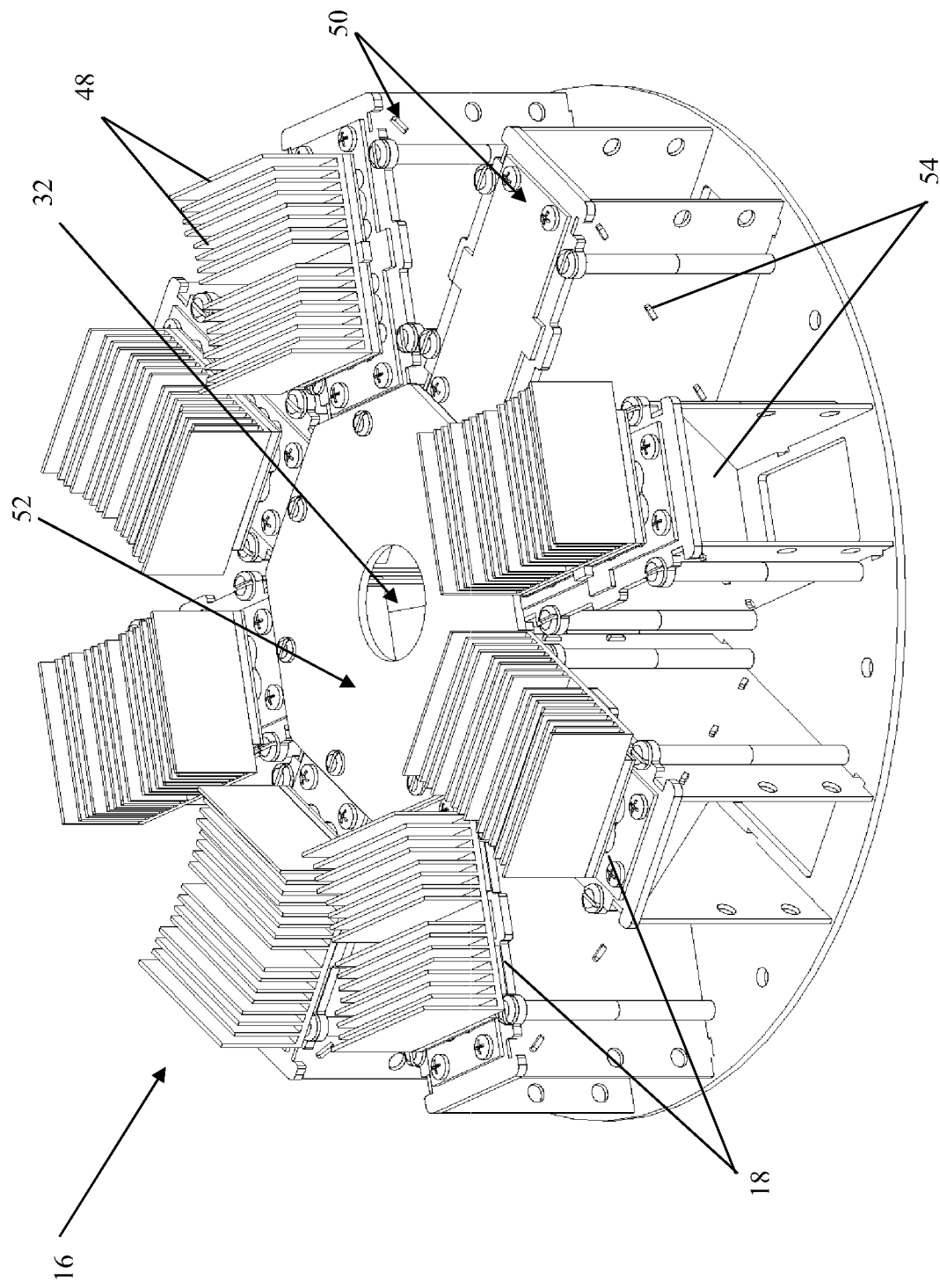
FIG. 7A is perspective side view of another embodiment of the light mixing capsule of the present invention.
Figure 7B:
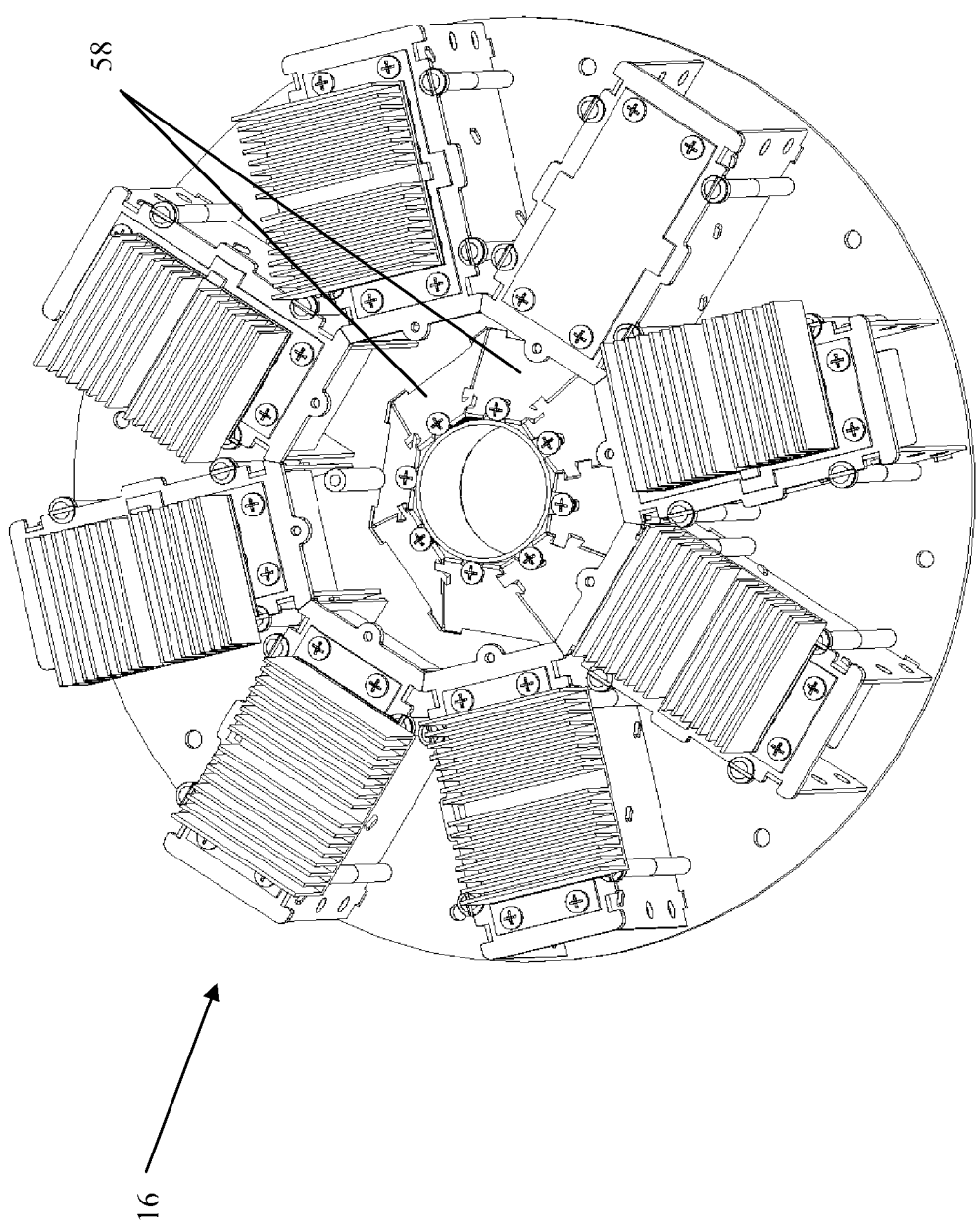
FIG. 7B is a perspective top view of the light mixing capsule of FIG. 7A but without a cover showing internal details of the capsule.
Figure 8:
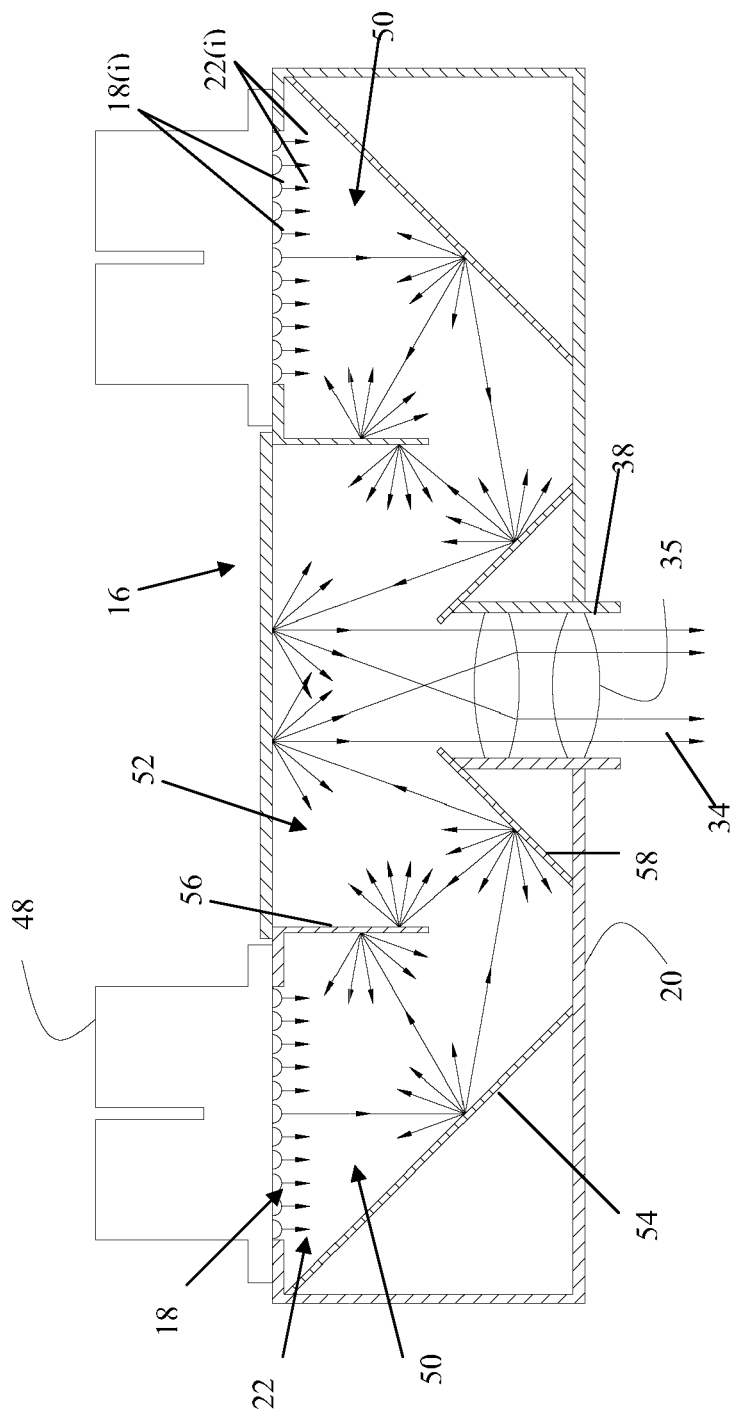
FIG. 8 is a cross-sectional view of the light mixing capsule of FIG. 7A.

Another embodiment of integrating light mixing capsule 16 is shown in FIGS. 7A, 7B and 8. As shown in FIGS. 7A and 7B, a plurality of primary light modules 18 are positioned atop integrating mixing capsule 16, which comprises a plurality of first mixing chamber 50 and at least one central mixing chamber 52 and is positioned on top of viewing chamber 12 (omitted for clarity). Cooling fins 48 are provided to carry heat away from primary light modules 18. Each primary light module 18 emits light beams 22, as described above. As shown in FIG. 7A, aperture 32 discussed above is optionally provided. Light beams 22, as best shown in FIG. 8, enter first mixing chamber 50 and are reflected off of first baffle wall 54. Light beams 22 are diffused after the first reflection throughout first chamber 50 and some are further reflected off of second baffle wall 56 or third baffle wall 58 (shown in FIGS. 7B and 8). Some reflected light may have multiple reflections among reflecting baffle walls 54, 56 and 58 and can be reflected back toward primary light modules 18. Eventually, reflected lights that originally emitted from primary light modules 18 enter central chamber 52. These lights are further reflected or mixed within central chamber 52 before exiting integrating light mixing capsule 16 at exit port 38 as mixed, uniform light 34. Optional exit optics 35, such as neutral density filters or lenses and other filters, can be placed within exit port 38 to further condition exiting light 34. Optical sensors, described below, can also be deployed within first mixing chambers 50 and/or central mixing chamber 52.

One advantage of the embodiment shown in FIGS. 7A, 7B and 8 is that light being mixed or reflected in central chamber 52 can re-enter first mixing chambers 50 for additional mixing before exiting integrating light mixing capsule 16. Another advantage of this embodiment is that a primary light module 18 can have multiple light sources 18(i), where each light source 18(i) can be different color stimuli of varying spectral power distribution (SPD) 22(i), that can be mixed in primary chambers 50. Any number of reflecting baffle walls can be employed. Preferably, the inner surfaces are also coated with reflective coating, as described above.

At least three primary light modules 18 should be used to represent colors in chamber 12. However, to have color gamut that is better than computer screens, which use either three primary colors (RGB), or printers, which use four primary colors (CMYK), at least five primary light modules should be used. As shown in FIGS. 1-2, seven primary light modules 18 are used. Preferably, at least eleven primary light modules are used or more preferably at least 16 primary light modules are used.

Figure 5:
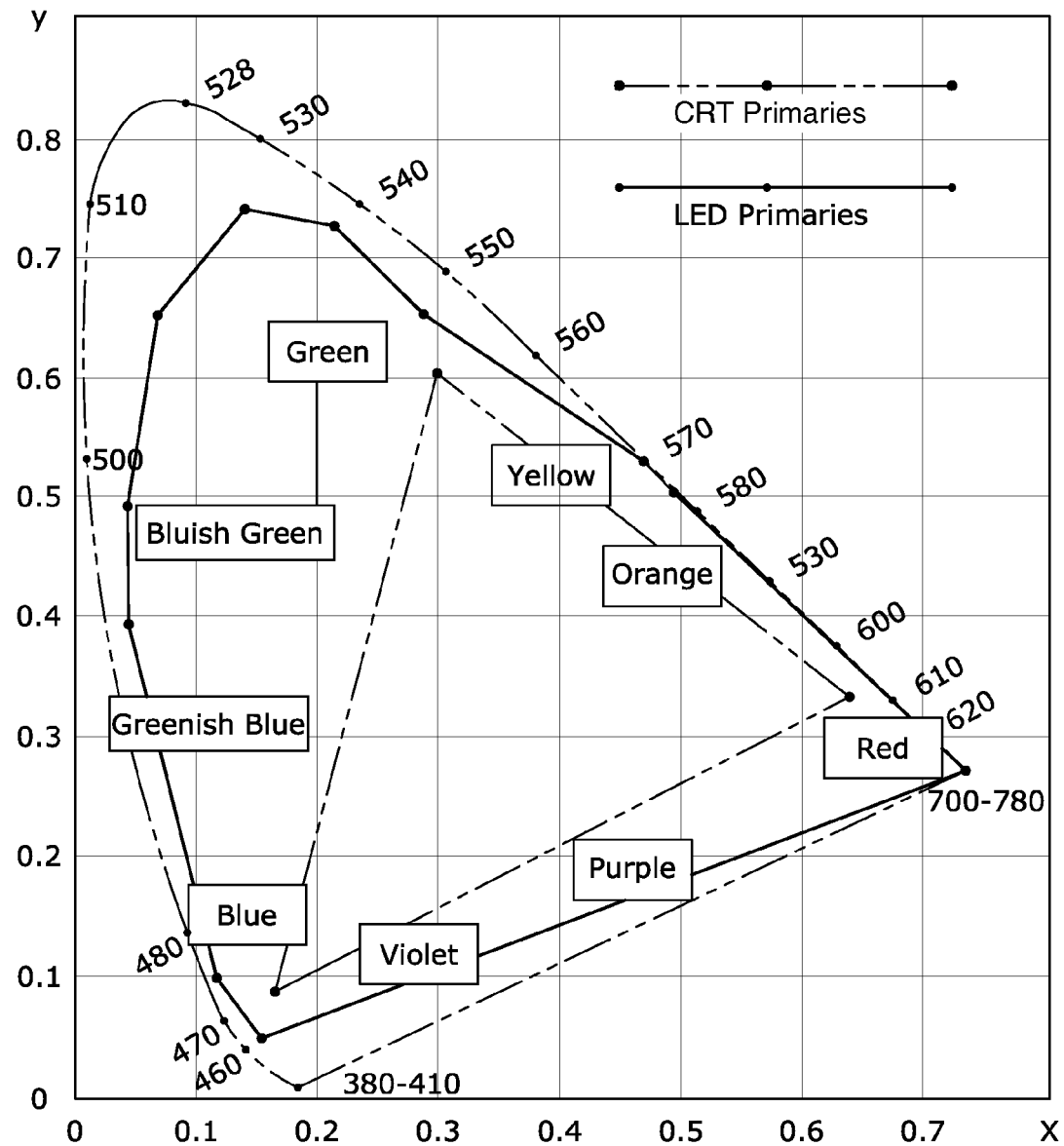
FIG. 5 is the 1931 CIE chromaticity diagram with two polygons representing displayable colors superimposed thereon.

FIG. 5 illustrates the well-known shark-fin shape of the 1931 CIE diagram. The shark-fin shape substantially represents all the colors visible to the human eye. The corners of the diagram are red, blue-magenta and green. The center of the diagram is white, which indicates that white light is the combination of all the individual perceived colors, and that white light can be divided into the other colors, e.g., by a prism. The inner triangle superimposed on the shark-fin has the three apices located in the red, green and blue regions of the CIE diagram. This RGB triangle represents the portion of the CIE diagram that can be displayed using the RGB convention. Since most computer screens utilize the RGB convention, a significant number of colors may not be displayed on computer screens. The outer irregular polygon superimposed on the CIE diagram encompasses the RGB triangle, and each apex of this polygon represents an individual color that can be produced by a device, e.g., an LED. As illustrated, eleven separate LEDs, each displaying a different color, can be used to expand the gamut of colors that can be displayed in chamber 12. In other words, the color LEDs are used to stretch the RGB triangle outward. Hence, color display device 10 in accordance with the present invention can display colors that may not be viewed on common RGB screens or CMYK printers, because a larger number of color LEDs can be employed in device 10. Hence, color display device 10 can display colors that simply cannot be viewed on computer screens.

The present invention is not limited to any number of LEDs or any particular color combination. Preferably at least five LEDs emitting different color light are used. More preferably, at least nine to eleven LEDs are used. Unique or different combinations of LEDs can be used to satisfy the particular application.

Color LEDs are widely available from many sources. Available LEDs can emit narrow bands of wavelengths or colors, as discussed in WO 2006/076211. LEDs are also available in broad bands, such as white LEDs. Broadband LEDs are generally produced by combining the entire available colored or narrow band LEDs to produce white or near white light. Broadband LEDs are commercially available through STMicroelectronics of Geneva, Switzerland, among other sources. When white LEDs and color LEDs are used, more colors can be displayed for the consumers and hence more paint colors can be displayed. Broad band LEDs that are less than white can be used in combination with other broad band LEDs that are also less than white, or with narrow band LEDs.

In an alternative embodiment, chamber 12 can be illuminated by LEDs, transistors or photocells constructed from organic polymers, available from Cambridge Display Technology or Plastic Logic Ltd. Polymer light emitting devices are disclosed in U.S. Pat. Nos. 5,807,627, 5,747,182, 5,653,914, 6,777,706, 6,723,811, 6,580,212, 6,559256, 6,498,049, and United States published patent applications 2004/0214039, 2004/0132226, 2004/0075381, 2004/0059077, 2003/0166810, 2003/0008991, and related patent references, including patent references sharing at least one inventor with the cited patent references. These references are incorporated by reference in their entireties.

In a preferred embodiment of the present invention, primary light modules 18 each has a bandwidth of about 25 nm, and the bandwidths of these light modules are spaced about 5 to about 10 nm apart. Fluorescent, incandescent, halogen, laser and other conventional light sources can also be used. Primary light modules can also be coated with fluorescent and phosphorous coatings. As discussed above, electromagnetic radiation in the invisible range can also be used as a primary light. In one example, ultraviolet radiation is emitted from a primary light module 18. The UV radiation can be converted by the coatings within mixing capsule 16, e.g., by altering its frequency, to change the UV radiation into blue light, to further increase the color gamut of the present invention. Other invisible electromagnetic radiations can also be changed to visible electromagnetic radiation by known methods.

In accordance with another aspect of the present invention, the color inconstancy effect can be minimized for the consumers. Color display device 10 can simulate the ambient light conditions that exist at the consumer's dwellings or offices. Simulated ambient light can be mixed with the primary lights, for example by introducing simulated ambient light through aperture 32 of curved reflector 30, discussed above. Also, one of the primary light modules 18 can be programmed or designed to emit simulated ambient light. As used herein simulated ambient light or simulated ambient condition includes simulated daylight, halogen, incandescent or fluorescent lights, other ambient lights, or combinations thereof. Furthermore, simulated ambient light can be diffused and introduced separately and directed to chamber 12.

Color display device 10's ability to change or control ambient light conditions can also minimize the effects of metamerism. Two or more dried paint samples can be placed within viewing chamber 12, and the simulated ambient light can be altered to show the consumers whether the color appearances of the paint samples remain the same, substantially the same or different, as the simulated ambient light changes.

An advantage of the present invention is that the consumers can be shown the same physical paint color under various simulated ambient conditions. For example, a paint color can be shown in daylight with color temperatures of 5000, 5500, 6500 or 7500 Kelvin, and simulated ambient light at sunrise or sunset can be displayed by adding a tungsten filament lamp (2856 Kelvin), these illumination sources can be mixed to arrive at a desirable ambient condition, so that the consumers can view the paint colors between cool (6500 Kelvin) and warm (2856 Kelvin). The consumers can view the same paint color at sunrise, mid-day, sunset or evening, to ascertain how a room would look throughout the day. Furthermore, the consumers can view how the paint may look in a sunny room versus a shady room, and may adjust the paint colors so that all the rooms in a dwelling may look substantially the same, if desired.

Primary light modules 18 and the other optical components are preferably controlled electronically by a computer or a central processing unit (collectively CPU). Among other things, the CPU controls the amount of luminance of each light module 18 by dimming the LEDs contained in the light modules 18. Dimming LEDs can be accomplished by pulse width modulation (PWM). PWM uses varying pulse widths to vary the percentage of "on" and "off" time of a LED to effect dimming. This typically occurs at high speeds to minimize flickering or strobing to the consumers. For example, dimming an LED at 25% can be achieved with PWM by pulsing the LED to the on position at 25 µs and to the off position for 75 µs, and so on.

Figure 6:
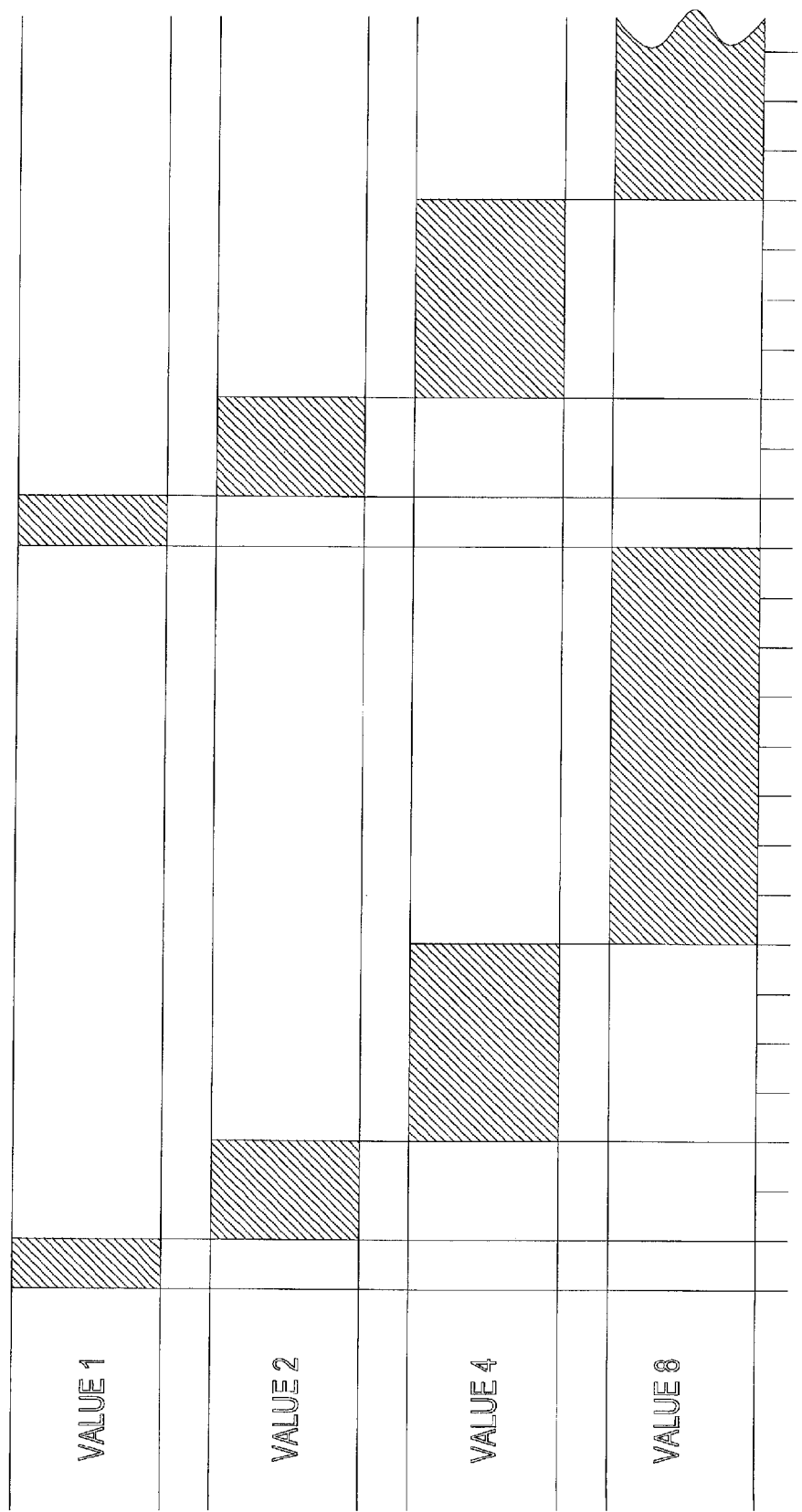
FIG. 6 is a graph showing the waves of pulses that can be used to dim the primary light modules.

In accordance with another aspect of the present invention, LED dimming can be accomplished by selectively adding a number of available waves of repeating pulses. As shown in FIG. 6, four exemplary waves of pulses are shown. The first wave has repeating pulses with a width of one unit (e.g., each unit=10 µs). The second wave is offset from the first wave and its pulses start when the pulses from the first wave end, and the repeating pulses from the second wave have a width of two units. The third and fourth waves are similarly constructed with the pulses from the third wave having a four unit width and the pulses from the fourth wave having an eight unit width. It is to be noted that these widths can be any convenient size. According to this method, the time duration of all the available pulses in one cycle is 15 units (eight+four+two+one). To dim a LED at ⅓ its luminance, only the first and third waves are used. To dim a LED at about ½ its luminance, either only the fourth wave or a combination of the first, second and third waves is used. This method is an improvement over PWM, because a LED can be quickly dimmed to any fraction of its luminance without reprogramming the timing circuit. The higher number of waves can produce more gradation in the dimming effect. All the waves can be used to drive a single LED or each wave can be used to drive a single LED.

Through dimming, the amount or intensity of emitting light from each light module 18 can be controlled and mixed in light mixing capsule 16, so that mixed, uniform light 34 of different colors 34 can be displayed in chamber 12. Neutral density filters can also be used to evenly reduce the intensity of the displayed colors.

The CPU may also execute a procedure for selecting groups of colors in harmony or emotion or coordination in accordance to a tintometric system. A suitable procedure is described in PCT publication no. WO 03/027958, which is incorporated herein by reference in its entirety. The CPU may also include voice activation command, keyboard, computer mouse, touch screen and other input/output devices to communicate with the consumers.

The CPU can create lightings or desirable spectral power distribution continuously to generate special or desirable colors and appearance effects of a physical complex picture or other physical objects characterized by a given set of spectral reflectance data. The present invention can predict the effect of color shifts by comparing the spectral power distribution (SPD) to the spectral reflectance data of the object colors.

The Spectral Reflectance Factor (R %) is the ratio of quantity of the radiant energy reflected from the test surface to the quantity of radiant energy reflected by the perfect white diffuser for a given wavelength based on the same illuminating and viewing geometry. Thus, without changing the SPD of the incident light, one can alter the color appearance of a test surface by changing its spectral quantity R %, e.g., a warmer sensation may be accomplished by increasing its R % at the longer wavelength (620-700 nm) by changing the prescription of the coating surface with more red paint.

SPD is the radiant energy quantity distributed over the visible wavelength range (~400-700 nm). This radiant energy may be originated from additive mixing of two or more light sources, e.g., the simulated ambient light or mixed light 34 that comes out of the mixing capsule 16, and its spectral content can be further modified via selective wavelength absorption or other techniques. After exiting mixing capsule 16, the modified mixed light 34 with a new SPD can create a new color sensation upon reaching viewing chamber 12. For example, without changing the R % of the test surface of an object, one can render the color appearance of the same test surface warmer by boosting the incident light's SPD with a higher radiant energy content at the red wavelength range (620-700 nm) e.g., adding a red LED light.

The SPD and the R % are two parameters that can be utilized to predict the effect of color shifts in the following manner. First, the test surface, e.g., surface 14 described above, has a constant R % but mixed light 34 has variable SPD. In other words, test surface 14 remains the same and mixed light 34 can be changed to produce various colors as described herein. Employing the inventive integrating light mixing capsule 16 and the various primary light sources 18 and other optical devices, the SPD of mixed light 34 incidents onto test surface 14 or a mock object, which in this example is white, to create a desired color appearance. This is possible because the R % of the test surface is known and the SPD of incident mixed light 34 is also known or can be controlled by the CPU. Alternatively, given a white (or colored) test surface, the CPU can compute the required SPD of the incident mixed light(s) 34 to render the test surface "warmer/cooler", "exciting/calming", "clean/dirty", "light/dark", etc. An important feature of this device is to allow customers to visualize the alternative color options for color decision.

Second, incident mixed light 34 has a constant SPD, but the test surface has a variable R %. The primary light sources 18 and the integrating light mixing capsule 16 are used to output a desired incident light SPD, which can simulate the customer's home lighting or can be simulated ambient light. The inventive system can help the customers to select the color chips, which serve as the test surfaces, with desired color appearance or with certain color emotions, e.g., "warmer/cooler", "exciting/calming", "clean/dirty", "light/dark", etc. A preferred feature of this device is to allow customers to visualize the alternative color options for color decision. Furthermore, paint manufacturers can customize the color prescription or formula to create the required R % property in order to create the desired color effect.

Both of these methods can be combined so that the incident mixed light 34 can be varied or controlled and the test surfaces 14 can also be varied, so that the test surface can have colors other than white.

The CPU can also control the cooling of the primary light sources 18. When LEDs are used, their SPD or color outputs are subject to aging and thermal drifts. Hence, it is desirable to control the temperature of the LEDs to control their color outputs. One way of controlling the temperature is by fins 48, shown in FIGS. 7-8, which is a passive cooling system and is not controlled by the CPU. Optical sensors such as spectral, luminosity and/or temperature sensors can be deployed and electronically connected to the CPU to measure the color or SPD output, the luminosity or the temperature of the LEDs. Electrical or electronic sensors, such as thermocouples or thermistors can also be used and be controlled by the CPU. Cooling fans, liquid coolant or any other known cooling mechanisms can be provided and/or controlled by the CPU to maintain the output and temperature of the LEDs at desirable levels. The cooling system can be housed in housing 20, shown in FIG. 1.

LED outputs are also susceptible to variation due to aging. The electronic control system described above can also employ the SPD and/or luminosity sensors to compensate for the aging effects. The electronic control can also compensate the balance and drive of the primary light sources based optical feedback and predictive data sets to maintain the desired mixed output. This compensates for non-linear chromatic to luminosity emitter relationships, aging and environmental effects, which include simulated ambient lighting conditions.

The integrating light mixing capsules 16, described above, have the ability to display accurately certain color, such as browns, by a wide dynamic brightness range of the primary light modules 18. This is achieved by a high turndown ratio in the electronic dimming circuits (e.g., 1:500) coupled with neutral density filters at the exit optics.

There are several CIE Chromaticity Diagrams: the CIE 1931 Chromaticity Diagram (based on two degree CIE Standard Observers) and the CIE 1964 Chromaticity Diagram (based on ten degree CIE Standard Observers). In 1976, CIE published two new uniform spaces: CIELAB and CIELUV. All these CIE recommendations can be used with the present invention. Other color order systems or color specifiers such as Pantone, Natural Color System, Munsell Color System, Hunter LAB system or the like, can also be used with the present invention. Some of these systems can be converted to the CIE diagram, e.g., the Munsell systems are convertible to CIE.

In accordance with one aspect of the present invention, each commercially available paint color from a palette, e.g., Benjamin Moore's color palette, is associated, calibrated or linked to a CIE colorimetric specification, and each device-dependent color is also associated or linked to a CIE colorimetric specification. Hence, each device-dependent color displayed in chamber 12 is associated with a paint color from the tens of thousands of commercially available paint colors.

Device 10 can be used at retailers, paint stores and other paint dispensers, trade shows, offices, restaurants, airports, train stations, and other public buildings.

As used herein, "true colors" or "device-independent colors" denote colors that are visible to the eyes, defined in CIE color space, without the need of a device, such as computer equipment, televisions, diodes, light emitting diodes (LEDs), projectors, computer displays, screens or the like. The "device-independent color space or profile connection color space" is based on the CIE 1931 standard colorimetric observer. This experimentally derived standard observer provides a very good representation of the human visual system with respect to color matching capabilities. Unlike device dependent color spaces (e.g., monitor RGB system), if two colors have the same CIE colorimetric specification, they will match if viewed under the same conditions as those defined for the CIE colorimetry. True colors of a surface include those that are visible when light reflects off that surface, or those that can be produced by pigmented compositions coated on the surface, such as paints and coatings. On the other hand, "device-dependent colors" are colors, defined in device color space, produced by the devices listed above. Typically, the device-dependent colors are produced within the devices by combinations of the spectral ranges within the visible radiation spectrum of electromagnetic radiation. The wavelengths of visible radiation spectrum range from below about 400 nm (violet) to above about 700 nm (red). In one example, the device-dependent colors can be created by combining different amount of the three primary colors: red (625-740 nm), green (520-565 nm) and blue (435-500 nm) or RGB, e.g., RGB computer monitors. The RGB convention represents approximate emission bands of wavelengths. Device-dependent colors can also be produced by mixtures of four process colors: cyan, magenta, yellow and black or CMYK, e.g., offset printing of color documents. The CMYK convention represents approximate absorption bands of wavelengths. Device-dependent colors based on RGB convention can be converted by known color management systems to CMYK convention and vice versa.

Figure 9:
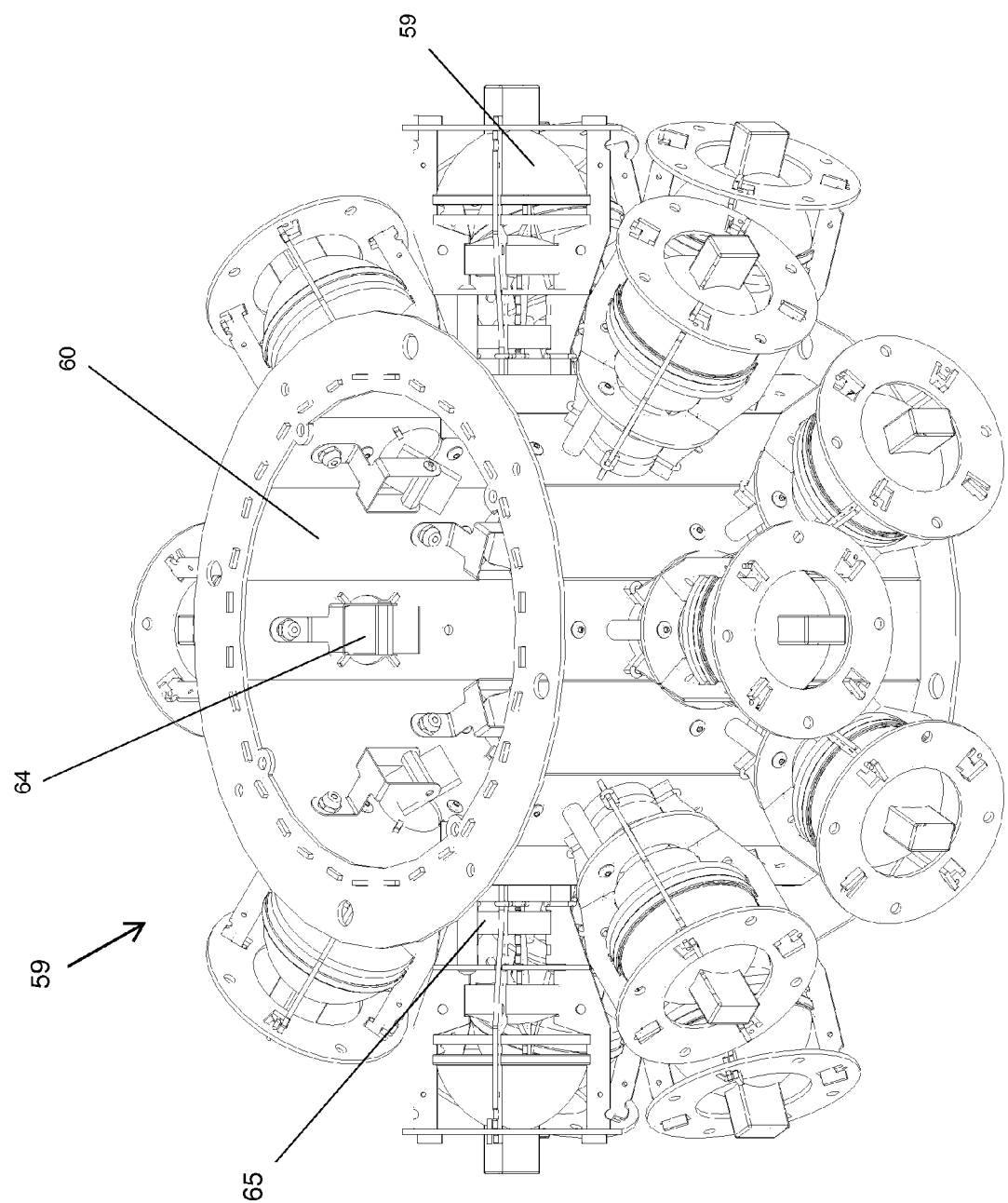
FIG. 9 is a perspective side view of another embodiment of a plurality of primary light modules radially surrounding an integrating light mixing chamber, according to an another embodiment of the present invention.
Figure 10:
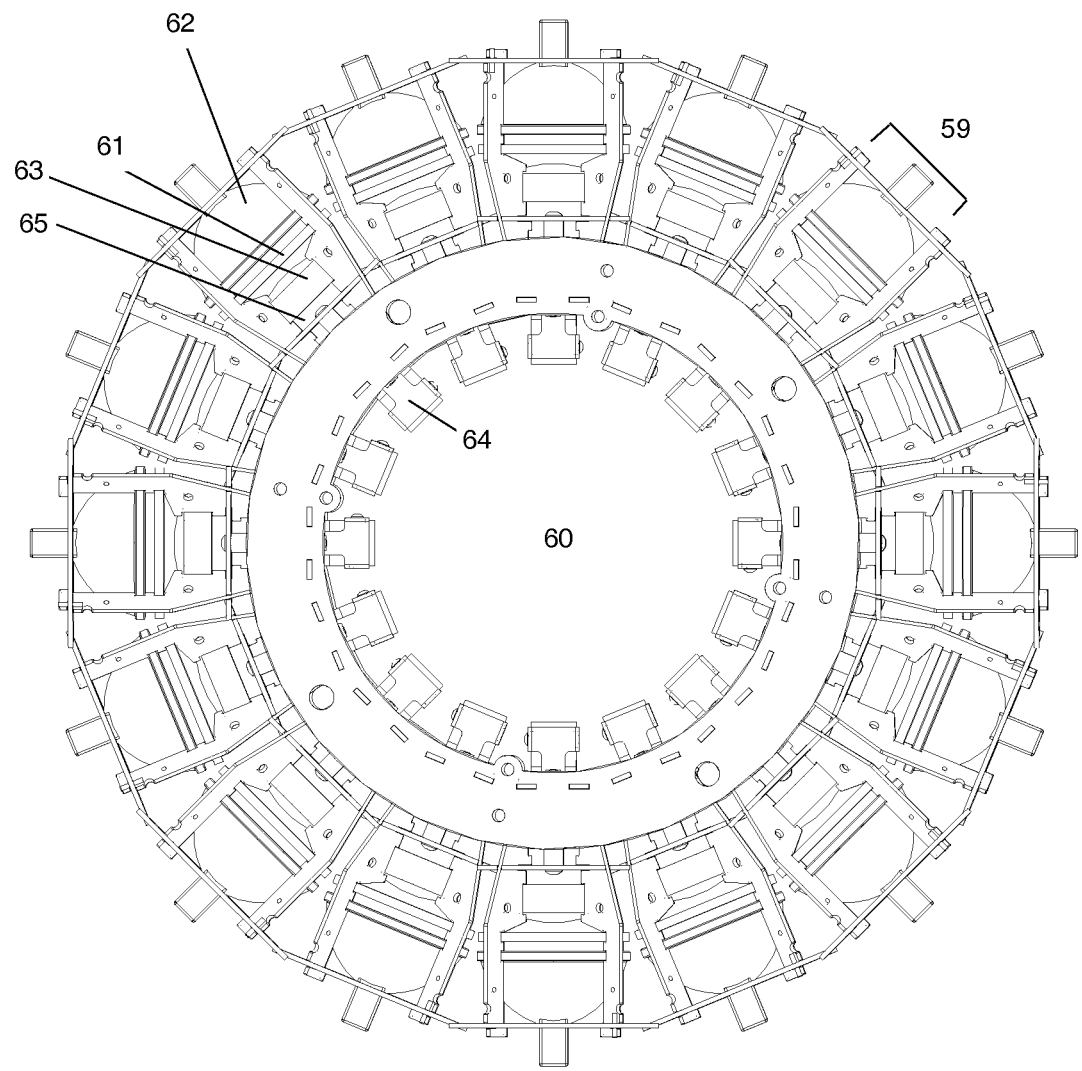
FIG. 10 is a top view of the embodiment depicted in FIG. 9.

FIGS. 9 and 10 depict an alternate embodiment of the present invention. As shown in FIGS. 9 and 10, a plurality of alternate primary light modules 59, which are another embodiment of primary light module 18 discussed above, are positioned radially around an integrating light mixing chamber 60, which is another embodiment of integrating light mixing capsule 16 in FIG. 4A. In this embodiment, all primary light modules 59 use a conventional lamp that produces a broad band light of the same or substantially the same color. Each primary module 59 has a unique narrow band filter 65, such that the light leaving each primary module 59 has a unique color or more specifically a unique primary color also known as a channel. Advantageously, in one aspect of the invention, a digital controller can simultaneously modulate two or more channels by the same amount as if they were "integrated" together. The primary light exiting each module 59 is directed by mirror 64 into mixing chamber 60 to be mixed similar to the other integrating light mixing chambers discussed herein.

Figure 11:
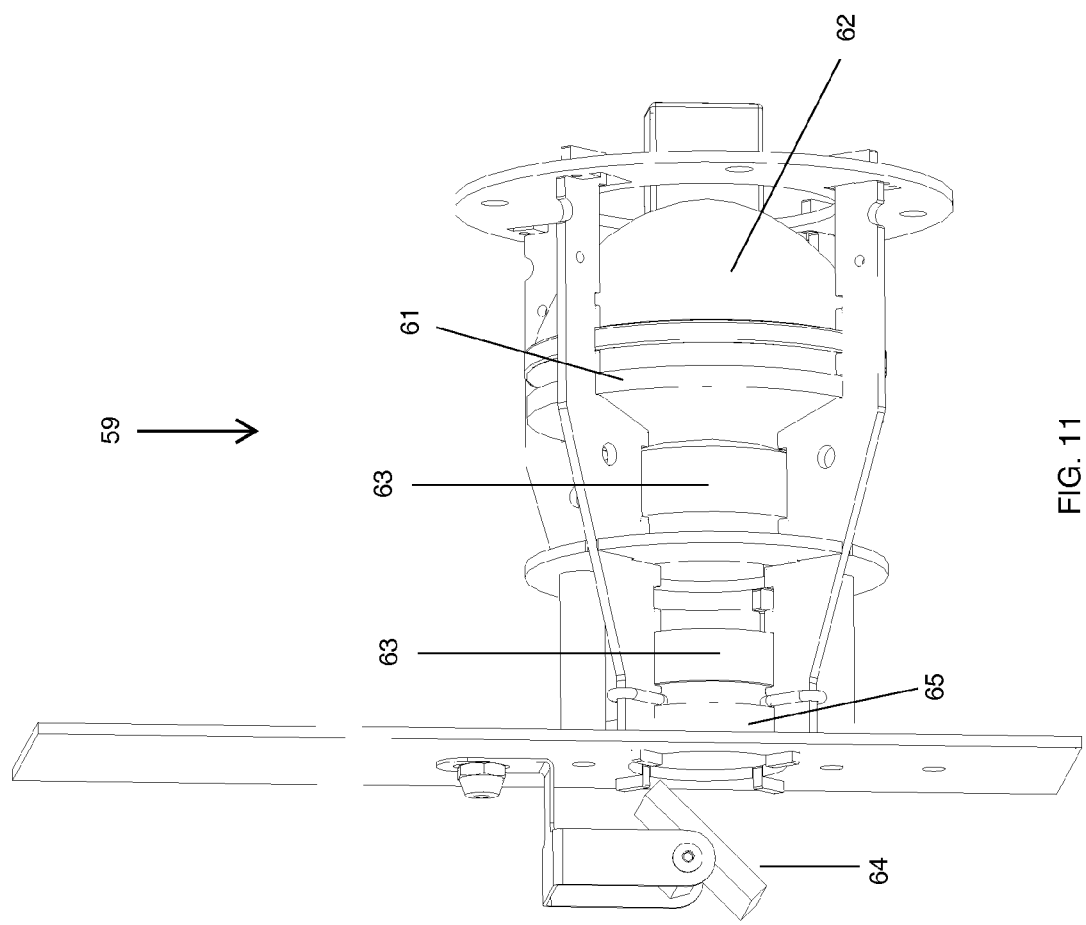
FIG. 11 is an enlarged view of the primary light module of FIGS. 9-10.

FIG. 11 illustrates an enlarged view of alternate primary light module 59, which uses a conventional light source or lamp 62, such as fluorescent, incandescent, halogen, laser and other conventional light sources. In a preferred embodiment, lamp 62 is a halogen lamp. The primary light module 59 comprises several optical devices that modulate light emitted from lamp 62. An infrared cut off filter 61 minimizes heat emitted from lamp 62. IR radiation does not contribute to visible colors and is known to have high thermal energy. Beam diameter reducing lenses 63 direct the lamp light onto optical filter 65. Advantageously, such beam diameter reducing lenses 63 produce light with a small physical envelope that is more compatible with optical filters 65 having a relatively small size.

The light emitted from lamp 62 is broad band, e.g., incandescent, halogen, fluorescent, and can be divided into narrower bands to represent distinct colors. Optical filters 65 are narrow band filters capable of dividing the broad band light from lamp 62 into a plurality of primary lights. Mirror 64 directs light to the interior of chamber 60 for integrating light mixing prior to it being projected onto the textured surface 14 of viewing chamber 12.

Figure 12:
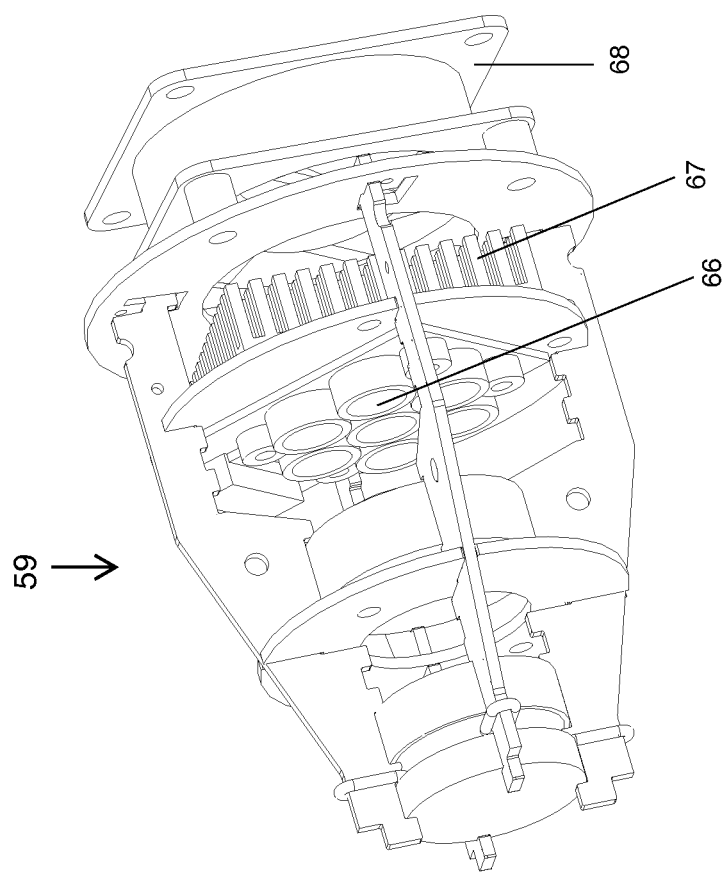
FIG. 12 is a perspective view of another embodiment of the primary light module of the present invention.

FIG. 12 shows another embodiment of alternate primary light module 59, which uses LED lamps 66 instead of conventional light sources. In this embodiment, the primary light module 59 further comprises a heat sink 67 and active cooling device 68 to keep LEDs cool, as discussed above. LED lamps 66 comprise a plurality of identical/similar monochromatic LEDs to boost radiant intensity output or white LEDs to produce a near-white light source. One advantage of using LED lamps 66 over conventional lamps shown in FIG. 11 is that the near white light has a wider frequency band and more primary colors can be divided therefrom.

In both FIGS. 11 and 12, the intensity of the light from lamp 62, 66 is modulated by a light controller via digital modulation means including, but not limited to, current modulation, pulse modulation, liquid crystal phase modulation, digital micromirror orientation modulation, and combinations thereof.

Figure 13:
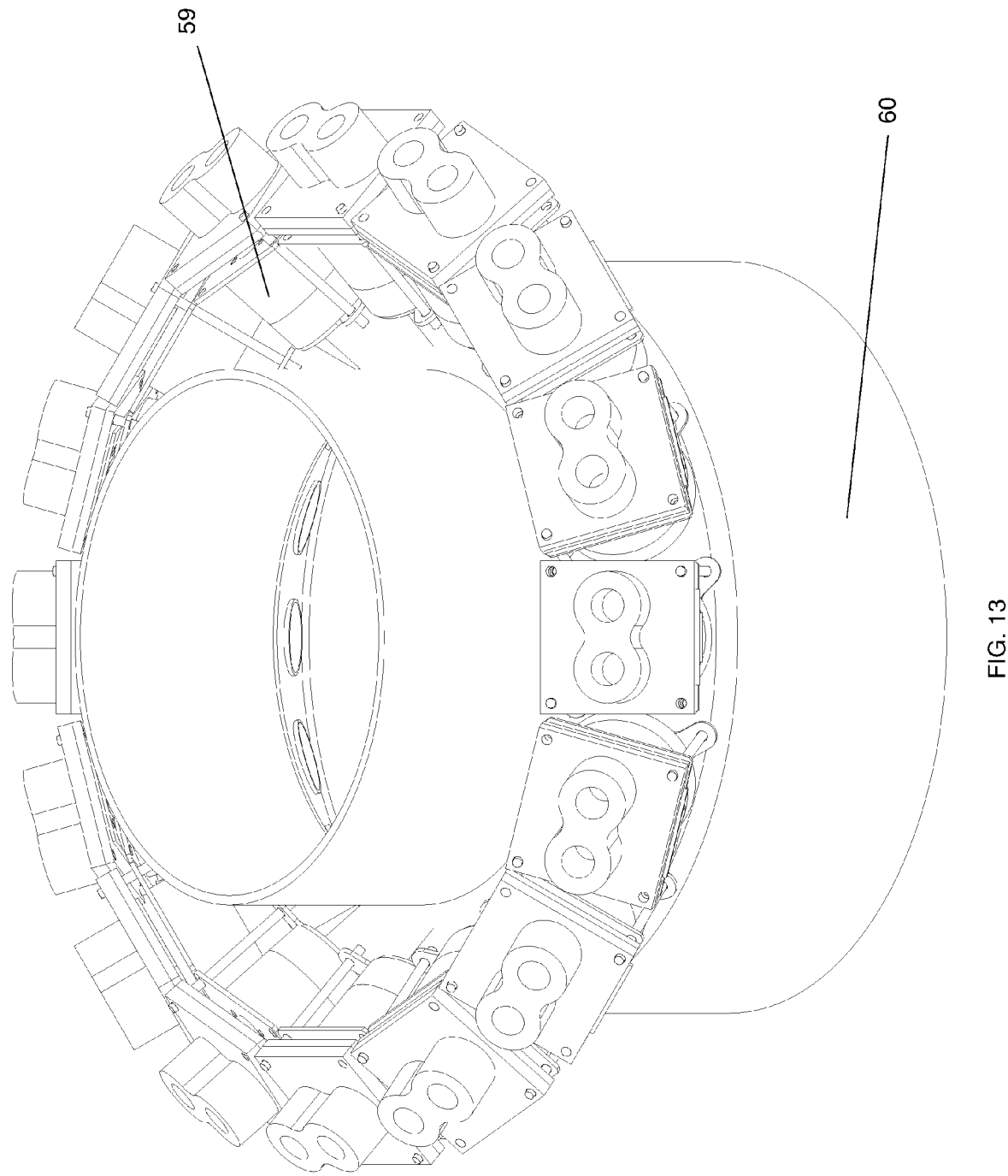
FIG. 13 is a perspective view of a plurality of primary light modules radially surrounding an integrating light mixing chamber, according to an another embodiment of the present invention.
Figure 14:
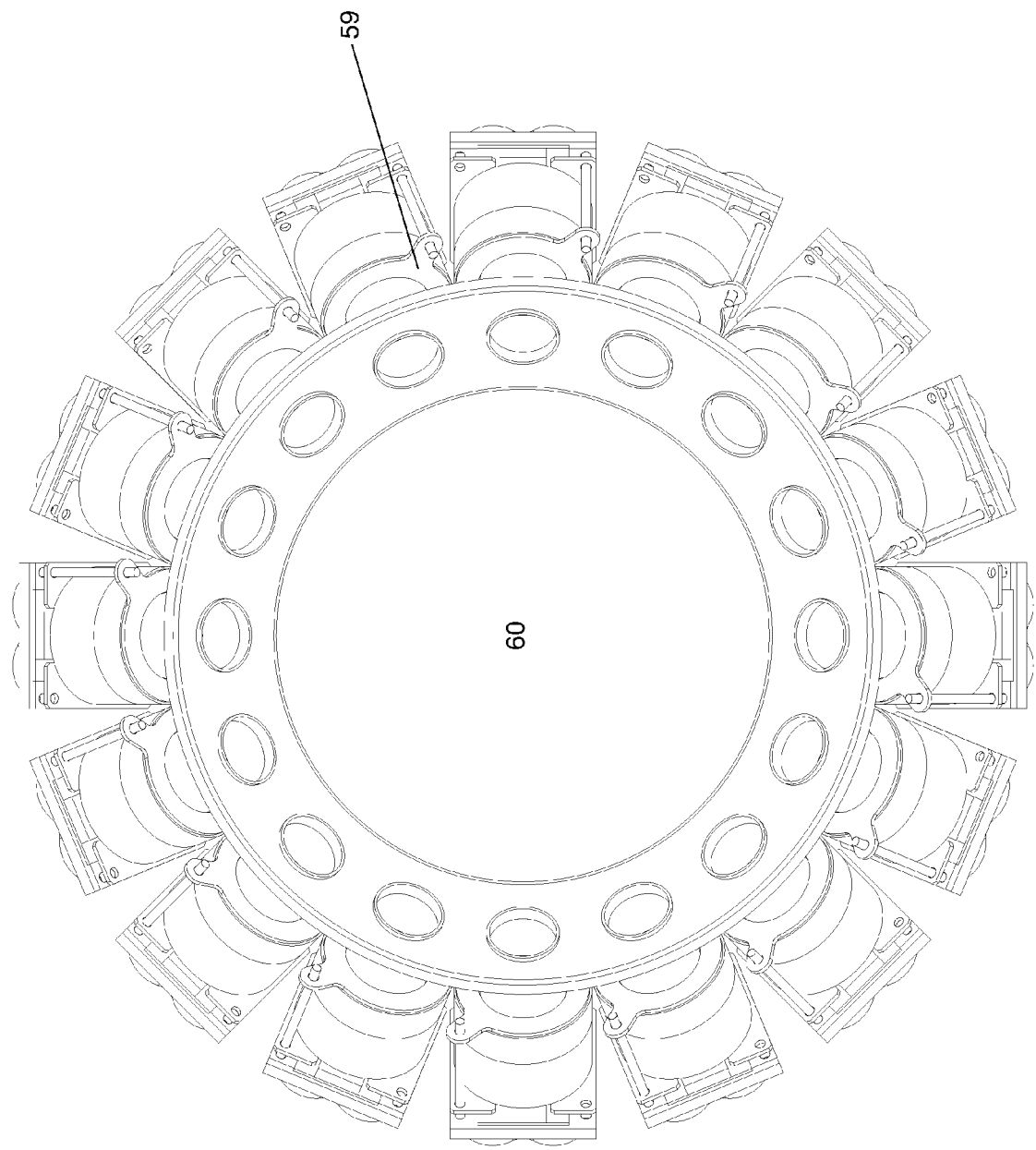
FIG. 14 is a bottom view of the embodiment depicted in FIG. 13.

FIG. 13 depicts an isometric view of another apparatus comprising primary light modules 59 and light mixing chamber 60, and FIG. 14 depicts a bottom view of such an apparatus. More particularly, a plurality of primary light modules 59 are positioned radially around integrating light mixing chamber 60. The primary light modules 59 are positioned at about a 45° angle, thereby directly focusing light on the reflective bottom of chamber 60. Mirror 64 is omitted in this embodiment, and primary light modules 59 can be angled at any desired angle. Moreover, as discussed in greater detail below, in an innovative aspect of the present invention, the plurality of primary light modules 59 comprise at least about 14, preferably at least about 16, or at least about 18, or at least about 24, or at least about 32 identical full broad band spectrum white LEDs, which can advantageously be used in conjunction with optical and digital modulation technologies to divide the white light into a broad range of narrow band light primaries. According to one aspect of the present invention, in order to boost radiant output intensity for a certain primary module 59, two or more modules 59 of the same primary can be connected together in parallel format. These identical white LEDs have the additional advantages of interchangeability, high efficiency, small size, high durability and long life span.

Figure 15:
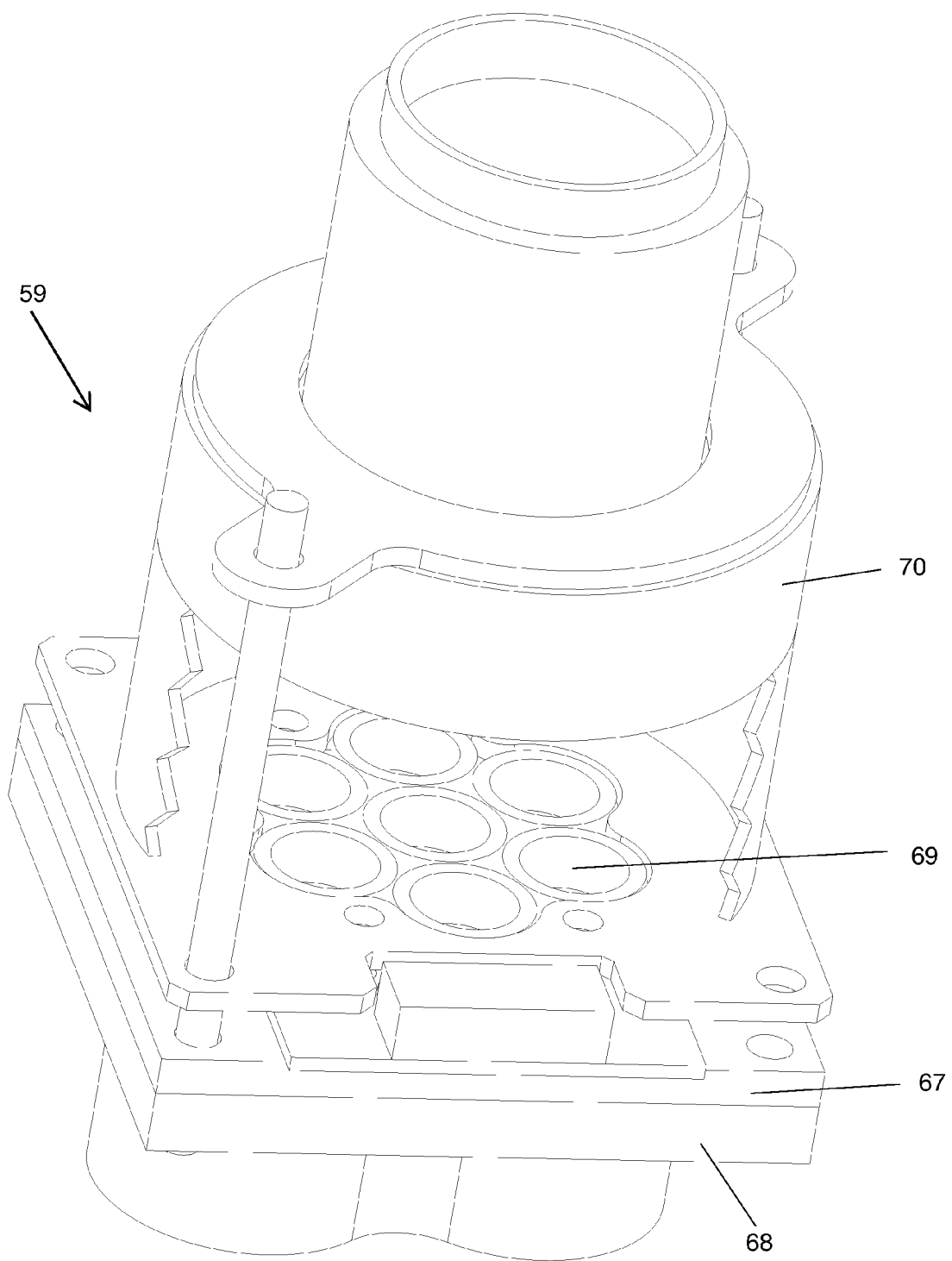
FIG. 15 is an enlarged view of the primary light module of FIGS. 13-14.

FIG. 15 depicts a primary light module 59, which is used in the apparatus depicted in FIGS. 13 and 14. This primary light module 59 comprises a primary light source 69, which preferably is a solid state light source such as a LED, or less preferably a conventional light source such a halogen lamp. Most preferably, as noted above, the primary light source 69 comprises a full spectrum white LED light source such as the Titan™ Series LED Lighting System (commercially available from Lamina Lighting, Inc. of Westampton, N.J.). The primary light module 59 further comprises a heat sink 67, an active cooling device 68, and a lens mount 70 storing narrow band filter 65 and optional lenses 63 similar to the primary module shown in FIG. 12. The lens mount 70 modulates by dividing primary light source 69 into unique narrow band primary color lights, and directs its primary light to the interior of chamber 60 for integrating light mixing prior to it being projected onto the textured surface 14 of viewing chamber 12. The lens mount 70 may also comprise several optical devices that modulate light emitted from source 69 including, but not limited to, a projection lens system, an optional infrared cut off filter, an optional UV cut off filter, and an optional optical filter.

Figure 16:
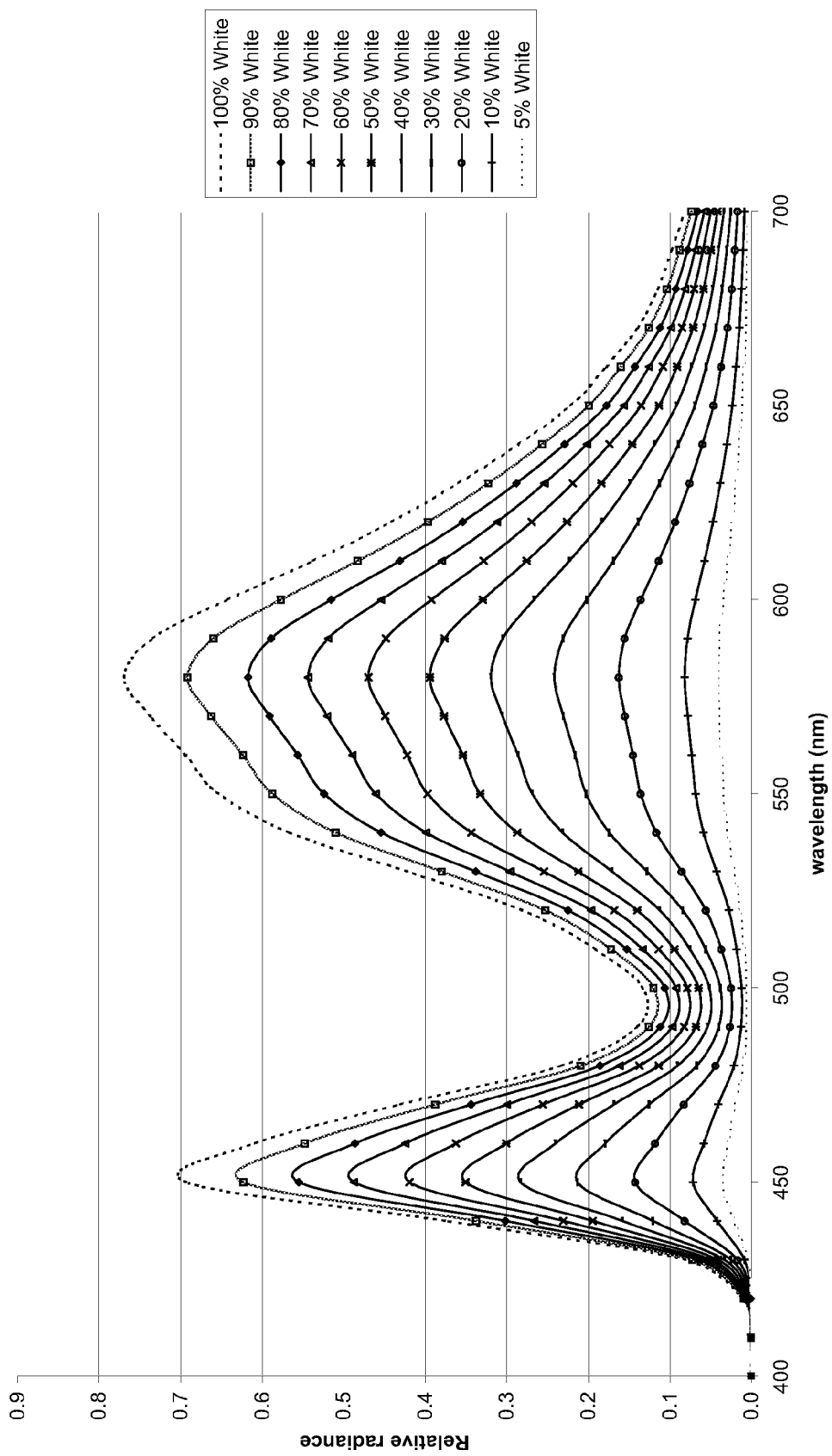
FIG. 16 is a graph showing the spectral power distribution curve of a full spectrum white LED at different levels of modulation.

Returning again to the discussion about the advantages of a full spectrum white LED, it is made up of a blue or UV LED with its envelope coated with a suitable mixture of phosphors. The LED light, in this case with blue or UV spectral quality, excites the phosphor coating that in turn creates light in the phosphor emission wavelength range. This results in a continuous full spectrum from about 400 nm to about 700 nm in the visible wavelength spectrum. By mixing the red, green and blue and other phosphors in various proportions, one can create light with a wide range of spectral characteristics from a very warm light to a very cool light with different color rendering power. FIG. 16 shows the relative spectral power distribution of a white LED, having a color temperature of about 4700 K, with its radiant power being modulated by a digital light controller at different levels from about 5% white to about 100% white. More particularly, the white LED is dimmable digitally with a wide dynamic range that can be achieved by modulating its pulse width and/or current. The radiant intensity at certain wavelengths, e.g., about 490 nm and beyond about 680 nm can be relatively weak. However, radiant intensity at these wavelengths can be supplemented with narrow LED sources having these wavelengths.

Figure 17:
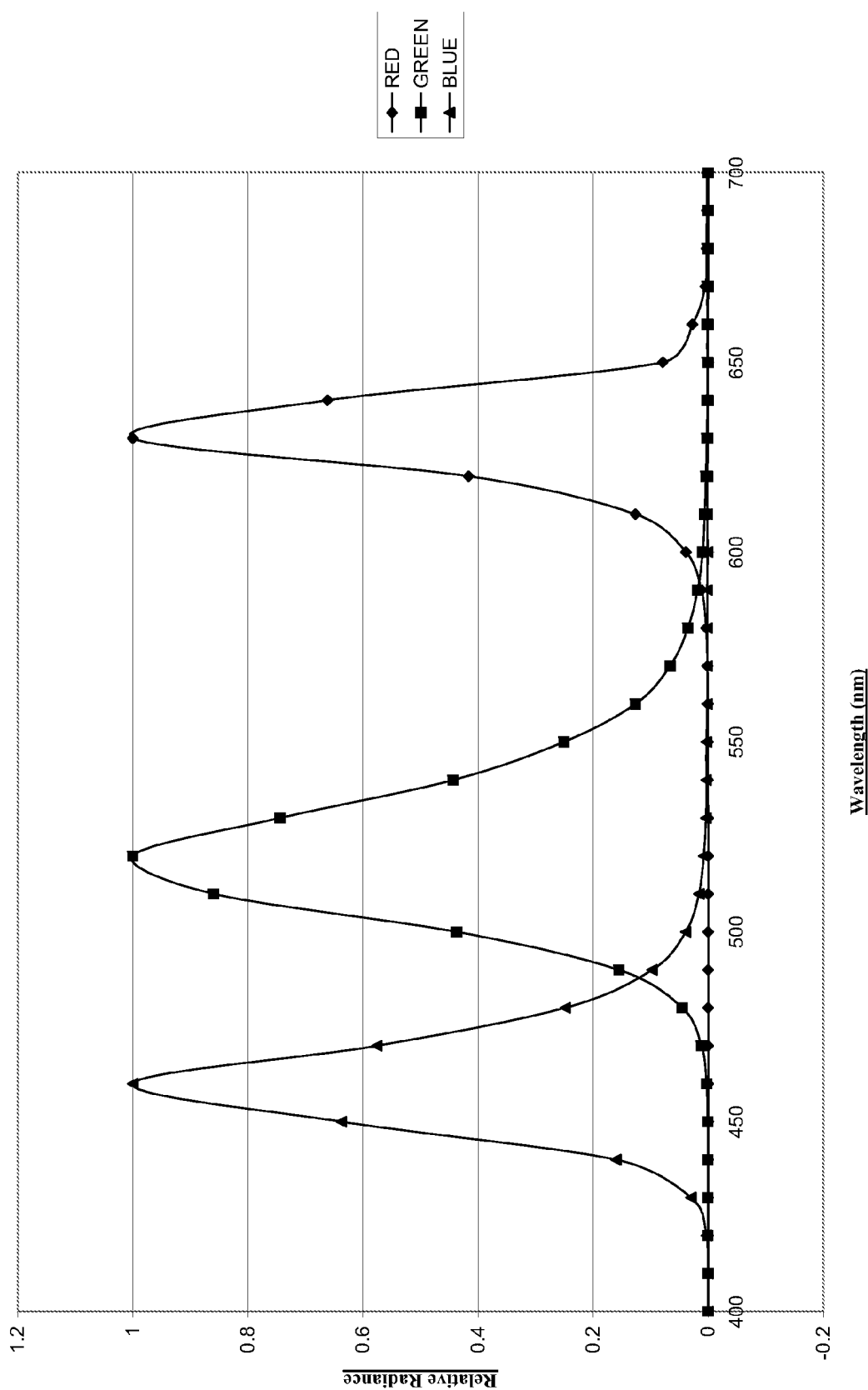
FIG. 17 is a graph showing the relative spectral power distribution curves of red, green, and blue LEDs comprising a tri-chromatic white LED.

The full spectrum white LED is different from the tri-chromatic white LED whose spectral power distribution curve is given in FIG. 17. The later mixes light from the red LED, green LED, and blue LED in different proportions to create white light with different color temperature. The radiant intensity of the tri-chromatic white LED is rich at/near to the wavelength(s) at the peak intensity of the RGB LEDs. The bandwidths at half power range from about 20 to about 35 nm depending on the individual LED. In other words, it is difficult to control the band width of the chromatic LED without further modulation by optical and/or digital means.

Because a full spectrum white LED emits radiant intensity in the entire visible wavelength range, it provides an opportunity to create highly desirable light primaries having peak wavelengths at a uniform interval (e.g., at most about 20 nm, preferably at most about 15 nm, and more preferably at most about 10 nm) from each other. This uniform "pitch" feature is an important factor in synthesizing color via additive mixing of the different light primaries. Advantageously, one can combine the full spectrum white LED with a chromatic LED having a peak intensity at one or more wavelengths where the white LED has weak intensity (e.g., about 490 nm and beyond about 680 nm), thereby boosting the relative spectral power at a broader range of wavelengths.

Optical modulation helps produce different light primaries confined to a narrow band of about 20 nm. More particularly, narrow band interference filters in lens mount 70, pass radiant energy with wavelengths within a certain range and reject wavelengths outside that range. Optical modulation is facilitated by the fact that LED illumination, unlike incandescent lamps, does not carry significant heat energy in its illuminating path. Rather, heat is generated at the LED junction in contact with the heat sink 67 where heat can be managed with an active cooling device 68. This is a preferred feature to help make optical modulation successful, as the presence of heat can be damaging to the optical narrow band interference filters.

Figure 18:
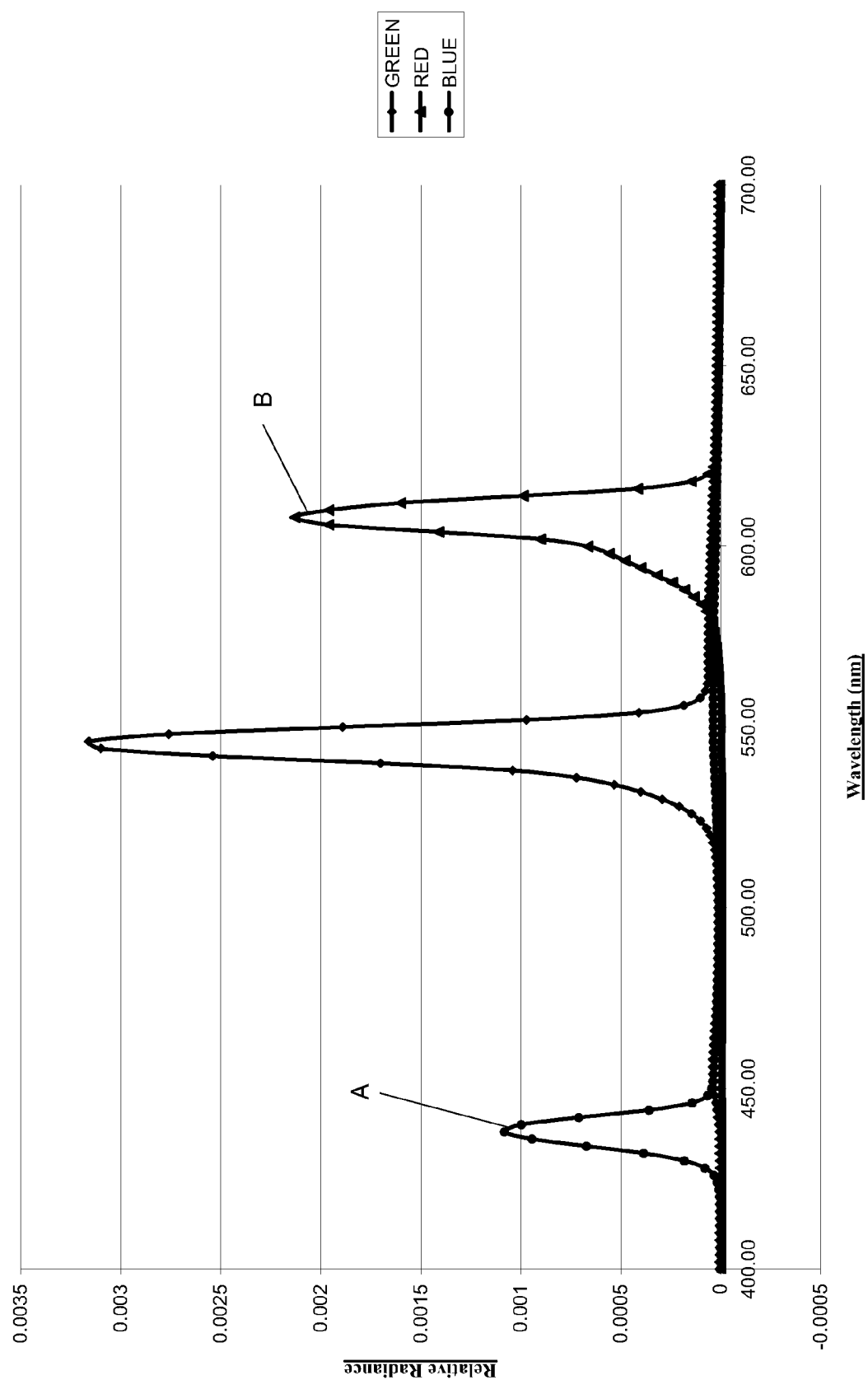
FIG. 18 is a graph showing the spectral power distribution curve of a full spectrum white LED optically modified by red, green, and blue narrow band filters.

FIG. 18 illustrates the spectral power distribution of a full spectrum white LED (see FIG. 16) is modulated into narrow band distributions using red, green and blue narrow band interference filters respectively. The band width (band pass) at half power is about 10 nm for all three cases. This shows the optical modulation method can control the spectral power distribution of each channel to have a uniform optical band pass property. This uniform band pass property preferably synthesizes white light or other chromatic light with significantly much more "smooth" spectral power distribution (SPD). Although FIG. 18 illustrates one preferred embodiment of a color primary channel, i.e., a white LED modulated by a narrow band pass filter, other embodiments are also possible. In other embodiments, a color primary channel can comprise a chromatic LED, a chromatic LED with a narrow band pass filter, a chromatic LED with a neutral density filter, or any combination of the aforementioned white LED and chromatic LED apparatuses.

Figure 19:
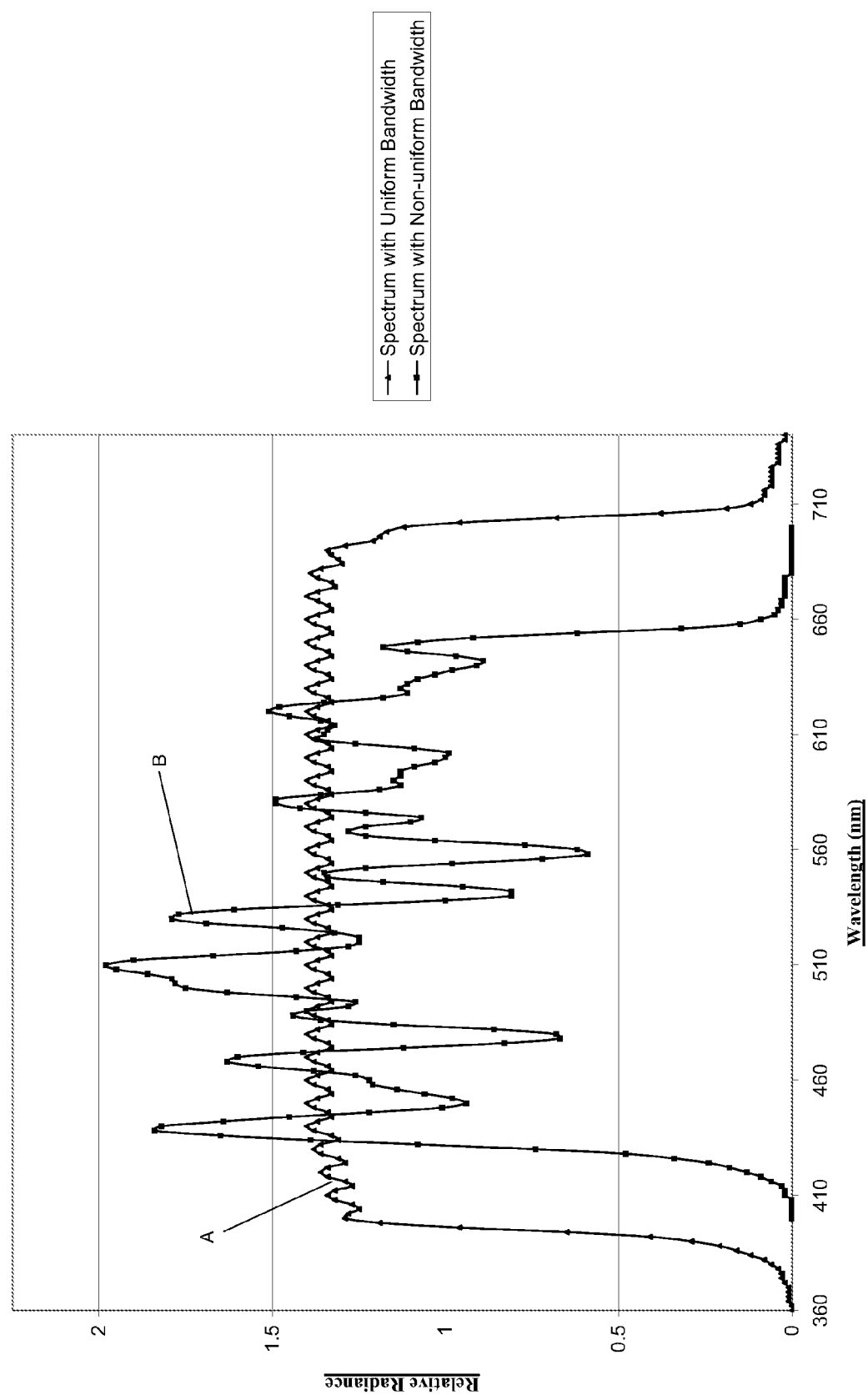
FIG. 19 is a graph showing the spectral power distribution curves composed with uniform and non-uniform bandwidth.

FIG. 19 illustrates this "smoothness" spectrum property. SPD curve A is composed of channels or lights with narrow band wavelength from about 400 to 700 nm at about 10 nm intervals. Each channel has an identical bandwidth at half power of about 10 nm. SPD curve B is composed of channels or lights with non-uniform band widths from about 400 nm to 700 nm. It is apparent that curve A, based on channels of uniform bandwidth, has a much smoother SPD than curve B, based on channels of non-uniform bandwidth. This "smoothness" spectrum property is important because most physical objects, such as paint chips, have a smooth spectral reflectance curve. Thus, in order to optimize matching the spectral stimulus of object colors with light, the channels making up the light should ideally have uniform bandwidth.

Prior to optical modulation by means of narrow band interference filters, the dimmable white LED light can undergo digital modulation. As noted above, there are several means including, but not limited to, current modulation, pulse modulation, liquid crystal phase modulation, digital micromirror orientation modulation, and combinations thereof. More particularly, it has been discovered that a wide dynamic range can be achieved by modulating its pulse width and/or current. The pulse width can vary from 0.5 µs to 300 ms in steps of 0.1 µs. A more detailed explanation of pulse width modulation is provided above. The current can vary from 0.5 mA to 2 A in steps of 0.5 mA. This kind of dynamic range is difficult to achieve with conventional lamps such as incandescent and fluorescent lamps. An example of dimming LEDs is discussed above, and shown in FIG. 6.

In a first stage, the plurality of primary light modules can each produce a light primary by a combination of optical and digital modulation of full spectrum white LED light. Subsequently, in a second stage, these modulated light primaries are additively mixed in integrating light chamber 16, 60. The intimately mixed light when projected onto a "mock" object can produce a color appearance matching a "target" color appearance in terms of spectral quality and gloss/sheen quality.

The concept of "appearance" matching is preferred to reflect the actual image observed by observers with normal color vision. For example, for a room painted with a single color using eggshell paint, an observer sees the entire room painted with a wide range of lighter and darker colors with more or less the same hue once the room light is switched on. This is because the observer sees the surface reflection (gloss/sheen with no color content), the body reflection (color content), as well as a wide range of mixed ratios of surface and body reflection. The surface reflection is the light specularly reflected from the paint surface (i.e., not modified by the paint colorant) whereas the body reflection is the light modified by the paint colorant and re-emerged from the paint that carries the color information. In addition, a "mock" object with a textured surface renders an additional dimension for appearance matching.

Innovatively, because one produces a broad range of light primaries (e.g., at least about 14, or at least about 16, or at least about 18, or at least about 24, or at least about 32), upon their mixing in the second stage, these light primaries can increase the available gamut of colors. As explained above, in connection with the discussion of FIG. 5, additional LED primaries stretch outward the boundaries of the irregular polygon denoting the visible color gamut.

Figure 20:
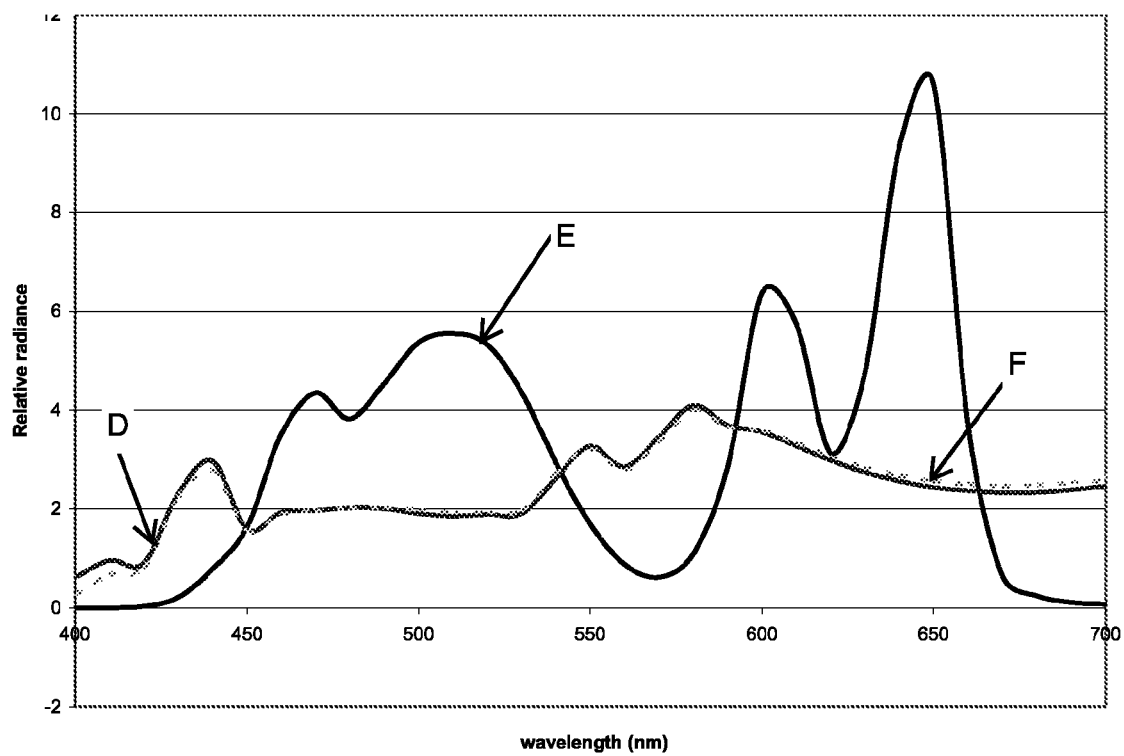
FIG. 20 is a graph showing the spectral power distribution curves of a target color and two sample colors.

FIG. 20 illustrates the advantage of a broad color gamut for purposes of matching a target color spectrum having a spectral power distribution indicated by curve D. When 6 LED color primaries (i.e., indigo, blue, cyan, green, yellow, and red channels) are utilized, the resultant color spectrum has a spectral power distribution indicated by curve E. Given that curves D and E are substantially different spectral curves, they represent a metameric match, i.e., the corresponding colors do not match under all viewing conditions. By contrast, when 32 LED primaries are utilized, the resultant color spectrum has a spectral power distribution indicated by a curve F. Given that curves D and F are substantially identical spectral curves, they represent a non-metameric match, i.e., the corresponding colors match under substantially all viewing conditions. Thus, there is an inverse relationship between the number of primaries and the degree of metamerism, i.e., increasing the number of primaries reduces metamerism. Advantageously, the present invention reduces the effects of metamerism by increasing the number of primaries.

While it is apparent that the illustrative embodiments of the invention disclosed herein fulfill the objectives stated above, it is appreciated that numerous modifications and other embodiments may be devised by those skilled in the art. Additionally, feature(s) and/or element(s) from any embodiment may be used singly or in combination with other embodiment(s) and steps or elements from methods in accordance with the present invention can be executed or performed in any suitable order. One such modification is that the system of the present invention can be scaled down to a hand held device that can project with LED light the device-dependent colors onto a wall. Such a scaled down version can be used in the buyers' homes. Another possible modification is to incorporate the system of the present invention with image projection device so that images or text in addition to color simulation can be projected onto screen 52. Moreover, another possible modification allows one to use any of the primary light modules with any of the light mixing capsules or light mixing chambers. Therefore, it will be understood that the appended claims are intended to cover all such modifications and embodiments, which would come within the spirit and scope of the present invention.

We claim:

1. An optical system comprising at least one broad band primary light source and a plurality of primary light modules each comprising a narrow band filter, wherein the narrow band filter modulates the spectral quality of the broad band light source into a narrow band primary light, wherein the emitted narrow band primary lights from the primary light modules comprise unique narrow band lights, wherein the emitted narrow band primary lights are directed to an integrating light mixing chamber, wherein the emitted narrow band primary lights are mixed within the integrating light mixing chamber to form a mixed exit light, and wherein the mixed exit light is projected on to a display surface to display a color on said surface, wherein the integrating light mixing chamber comprises a plurality of first mixing chambers and at least one central mixing chamber and wherein at least one first mixing chamber is associated with only a single emitted narrow band primary light, and wherein each first mixing chamber comprises a plurality of reflecting baffle surfaces.

2. The optical system of claim 1, wherein the emitted narrow band primary lights are reflected between the first mixing chambers and the central mixing chamber prior to exiting the integrating light mixing chamber.

3. The optical system of claim 1, wherein the reflecting baffle surfaces inside the integrating light mixing chamber are treated to increase the mixing of the emitted primary light.

4. The optical system of claim 3, wherein the surfaces are matted.

5. The optical system of claim 4, wherein the surfaces are coated with barium sulfate or titanium dioxide.

6. The optical system of claim 1, wherein the display surface forms a portion of a display chamber.

7. The optical system of claim 6, wherein the optical system is positioned adjacent to the display chamber.

8. The optical system of claim 1 further comprising a cooling system to regulate the output of the emitted primary lights.

9. The optical system of claim 8, wherein the cooling system comprises fins.

10. The optical system of claim 9, wherein the cooling system comprises sensors connected to a controller.

11. The optical system of claim 1 further comprising simulated ambient light.

12. The optical system of claim 11, wherein the simulated ambient light comprises simulated daylight, halogen, incandescent or fluorescent light or combinations thereof.

13. The optical system of claim 11, wherein one of the primary light sources emits simulated ambient light.

14. The optical system of claim 11, wherein the simulated ambient light is varied by a controller.

15. The optical system of claim 1, wherein the display surface is curved.

16. The optical system of claim 1 further comprising a three-dimensional object with at least one curved surface to receive the mixed exit light.

17. The optical system of claim 1 further comprising at least one optical device to condition the mixed exit light.

18. The optical system of claim 17, wherein the optical device comprises a neutral density filter, a center gradient filter, a spectral modification filter, a projection lens with an internal beam restriction mask or adjustable aperture.

19. The optical system of claim 1, wherein the display surface is textured to simulate a paint finish.

20. The optical system of claim 1, wherein the display surface is a diffusing surface.

21. The optical system of claim 1, wherein the integrating light mixing chamber further comprises at least one baffle that locates therewithin and prevents the emitted primary lights from exiting the integrating light mixing chamber without reflecting from the baffle.

22. The optical system of claim 1, wherein at least one of the reflecting baffle surfaces is formed by an internal member to the integrating light mixing chamber.

23. An optical system comprising at least one broad band primary light source and a plurality of primary light modules each comprising a narrow band filter, wherein the narrow band filter modulates the spectral quality of the broad band light source into a narrow band primary light, wherein the emitted narrow band primary lights from the primary light modules comprise unique narrow band lights, wherein the emitted narrow band primary lights are directed to an integrating light mixing chamber, wherein the emitted narrow band primary lights are mixed within the integrating light mixing chamber to form a mixed exit light, and wherein the mixed exit light is projected on to a display surface to display a color on said surface,
wherein integrating light mixing chamber comprises a plurality of reflecting baffle surfaces that form a plurality of first mixing chambers and at least one central mixing chamber.

24. The optical system of claim 23, wherein the integrating light mixing chamber further comprises at least one baffle that locates therewithin and prevents the emitted primary lights from exiting the integrating light mixing chamber without reflecting from the baffle.

25. The optical system of claim 24, wherein the integrating light mixing chamber has an entrance port and an exit port and the baffle is dimensionally larger than the entrance port and is located between the entrance port and the exit port.

26. The optical system of claim 25, wherein the integrating light mixing chamber is a polyhedron.

27. The optical system of claim 25, wherein the baffle comprises a dome portion.

28. The optical system of claim 25, wherein the baffle comprises a pointed portion.

29. The optical system of claim 25, wherein the baffle is connected to the integrating light mixing chamber by a plurality of legs.

30. The optical system of claim 23, wherein the emitted narrow band primary lights have a peak wavelength at a uniform interval of at most about 20 nm.

31. The optical system of claim 23, wherein the at least one broad band primary light source is selected from the group consisting of fluorescent, incandescent, halogen, laser, white LED, chromatic LED light, and combinations thereof.

32. The optical system of claim 31, wherein the at least one broad band primary light source comprises different broad band light sources.

33. The optical system of claim 31, wherein the at least one broad band primary light source comprises identical broad band light sources.

34. The optical system of claim 33, wherein the at least one broad band primary light source comprises white LED light.

35. A method for appearance matching a color comprising the steps of:
(a) providing an optical system comprising a plurality of primary light modules and supplying at least one broad band light source to the plurality of light modules;
(b) modulating the at least one broad band light source supplied to the primary light sources into narrow band primary lights, wherein the narrow band primary lights comprise unique narrow band lights;
(c) dimming at least one narrow band primary light;
(d) mixing the unique narrow band primary lights in an integrating light mixing chamber to form a mixed exit light, wherein the integrating light mixing chamber comprises a plurality of reflecting baffle surfaces that form a plurality of first mixing chambers and at least one central mixing chamber; and
(e) projecting the mixed exit light on to a display surface to display a color on said surface.

36. The method of claim 35, wherein the narrow band primary lights comprise a peak wavelength at a uniform interval of at most about 20 nm.

37. The method of claim 35 further comprising a step (f) of returning to step (b) if the display surface does not have an appearance matching a target appearance.

* * * * *